United States Patent

MacDonald et al.

(10) Patent No.: US 8,937,303 B2
(45) Date of Patent: Jan. 20, 2015

(54) ORGANIC ELECTROLUMINESCENT DEVICE

(75) Inventors: James Matthew MacDonald, Oakleigh South (AU); Kazunori Ueno, Burwood (AU); Karl Peter Weber, Surrey Hills (AU); Tadahiko Hirai, Mount Waverley (AU); Juo-Hao Li, Kaohsiung (TW)

(73) Assignee: Commonwealth Scientific and Industrial Research Organisation (AU)

( * ) Notice: Subject to any disclaimer, the term of this patent is extended or adjusted under 35 U.S.C. 154(b) by 0 days.

(21) Appl. No.: 13/880,903

(22) PCT Filed: Oct. 21, 2011

(86) PCT No.: PCT/AU2011/001344
§ 371 (c)(1),
(2), (4) Date: Apr. 22, 2013

(87) PCT Pub. No.: WO2012/051667
PCT Pub. Date: Apr. 26, 2012

(65) Prior Publication Data
US 2013/0264554 A1    Oct. 10, 2013

(30) Foreign Application Priority Data

Oct. 22, 2010 (AU) ............................ 2010904715
Sep. 13, 2011 (AU) ............................ 2011903758

(51) Int. Cl.
*H01L 33/00* (2010.01)
*H01L 27/15* (2006.01)
(Continued)

(52) U.S. Cl.
CPC .... *H01L 51/0067* (2013.01); *C09K 2211/1088* (2013.01); *H05B 33/10* (2013.01);
(Continued)

(58) Field of Classification Search
USPC .............. 257/40, 59, 102, 103, 690, E51.028, 257/E51.044, E51.049, E51.051; 252/301.16, 301.35; 313/502, 504, 313/506; 428/690, 917; 548/312.1, 313.1, 548/315.1
See application file for complete search history.

(56) References Cited

U.S. PATENT DOCUMENTS

| | | | |
|---|---|---|---|
| 4,539,507 | A | 9/1985 | VanSlyke et al. |
| 4,720,432 | A | 1/1988 | VanSlyke et al. |

(Continued)

FOREIGN PATENT DOCUMENTS

| | | |
|---|---|---|
| CN | 101665463 A | 3/2010 |
| ES | 2 232 286 A1 | 5/2005 |

(Continued)

OTHER PUBLICATIONS

International Search Report for corresponding International Patent Application No. PCT/AU2011/01344 (mailed Jan. 5, 2012).

(Continued)

*Primary Examiner* — Dao H Nguyen
(74) *Attorney, Agent, or Firm* — Merchant & Gould P.C.

(57) ABSTRACT

An organic electroluminescent device comprising: a pair of electrodes comprising an anode and a cathode, and one or more layers of organic compound arranged between the pair of electrodes, wherein the organic compound layer, or one or more of the organic compound layers, comprises a compound represented by a substituted imidazole. The substituents on the imidazole ring may be selected from a range of suitable substituents, including: substituted or unsubstituted aryl groups, substituted or unsubstituted heterocyclic groups, substituted or unsubstituted alkyl groups or cyano groups. In various aspects of the invention, at least one of the substituent groups may be a substituted or unsubstituted imidazole or thiophene group.

19 Claims, 2 Drawing Sheets

(51) Int. Cl.

| | | |
|---|---|---|
| *C07D 233/54* | (2006.01) | |
| *H05B 33/10* | (2006.01) | |
| *C07F 7/08* | (2006.01) | |
| *H01L 51/00* | (2006.01) | |
| *C07D 403/14* | (2006.01) | |
| *C07D 405/14* | (2006.01) | |
| *C07F 9/6506* | (2006.01) | |
| *C07D 233/61* | (2006.01) | |
| *C07D 401/14* | (2006.01) | |
| *C07D 417/14* | (2006.01) | |
| *C07D 487/16* | (2006.01) | |
| *C07D 409/14* | (2006.01) | |
| *C09K 11/06* | (2006.01) | |
| *H01L 51/50* | (2006.01) | |

(52) U.S. Cl.
CPC .......... *C07F 7/0818* (2013.01); *C07D 403/14* (2013.01); *C09K 2211/1011* (2013.01); *C07D 405/14* (2013.01); *C07F 9/65061* (2013.01); *H01L 51/0072* (2013.01); *C07D 233/61* (2013.01); *C07D 401/14* (2013.01); *C09K 2211/1044* (2013.01); *H01L 51/0085* (2013.01); *C09K 2211/1037* (2013.01); *C09K 2211/1029* (2013.01); *C07D 417/14* (2013.01); *C07D 487/16* (2013.01); *H01L 51/5016* (2013.01); *C09K 2211/1007* (2013.01); *C09K 2211/1014* (2013.01); *C07D 409/14* (2013.01); *C09K 2211/1092* (2013.01); *C09K 11/06* (2013.01); *H01L 51/0059* (2013.01); *Y10S 428/917* (2013.01)
USPC .............. 257/40; 257/59; 257/102; 257/103; 257/690; 257/E51.028; 257/E51.044; 257/E51.049; 257/E51.051; 252/30.16; 252/301.35; 313/502; 313/504; 313/506; 428/690; 428/917; 548/312.1; 548/313.1; 548/315.1

(56) References Cited

U.S. PATENT DOCUMENTS

| | | | |
|---|---|---|---|
| 4,853,383 | A | 8/1989 | Baldwin et al. |
| 4,885,211 | A | 12/1989 | Tang et al. |
| 5,247,190 | A | 9/1993 | Friend et al. |
| 5,514,878 | A | 5/1996 | Holmes et al. |
| 5,672,678 | A | 9/1997 | Holmes et al. |
| 6,355,665 | B1 * | 3/2002 | Tozer et al. ............... 514/400 |
| 6,436,559 | B1 | 8/2002 | Ueno et al. |
| 6,830,828 | B2 | 12/2004 | Thompson et al. |
| 7,371,737 | B2 * | 5/2008 | Koch et al. ............... 514/45 |
| 7,646,011 | B2 * | 1/2010 | Lee et al. ............... 257/40 |
| 7,919,773 | B2 * | 4/2011 | Kawakami et al. ............... 257/40 |
| 2008/0265758 | A1 * | 10/2008 | Han et al. ............... 313/504 |
| 2012/0021354 | A1 * | 1/2012 | Fujie et al. ............... 430/270.1 |
| 2013/0277652 | A1 * | 10/2013 | Seo et al. ............... 257/40 |

FOREIGN PATENT DOCUMENTS

| | | |
|---|---|---|
| JP | 63-276054 A | 11/1988 |
| JP | 2001-143871 A1 | 5/2001 |
| JP | 2003-519432 A1 | 3/2003 |
| JP | 2007-243101 A | 9/2007 |
| WO | WO 00/47194 A2 | 8/2000 |
| WO | WO 02/083111 A2 | 10/2002 |
| WO | WO 2005/047281 A1 | 5/2005 |
| WO | WO 2006/097030 A1 | 9/2006 |
| WO | WO 2010/138791 A1 | 12/2010 |
| WO | WO 2010/149968 A1 | 12/2010 |
| WO | WO 2011/031904 A1 | 3/2011 |
| WO | WO 2011/031934 A1 | 3/2011 |

OTHER PUBLICATIONS

Walker et al., Synthesis, characterization, and surface studies of conjugated polymers possessing 2,2'-biimidazole moieties, *Canadian Journal of Chemistry*, 87(6); 729-737 (2009).
Toba et al., "Electrochemical Preparation of a π-Conjugated Polymer having Imidazole Group 23 and Its pH-Responsive Functionality", *Japanese Journal of Applied Physics*, 47(2);1371-1373 (2008).
Murata et al., "Hydrogen-Bond Architectures of Protanated 4,4'-Biimidazolium Derivatives 24 and Oligo(imidazolium)s in Charge-Transfer Salts with Tetracyanoquinedimethane", *Crystal Growth & Design*, 8(8): 3058-3065 (2008).
Morita et al., "Novel Oligoimidazoles for Hydogen-bonded Charge-Transfer Complexes", *Mol. Cryst, Liq. Cyrst.*, 379: 83-88 (2002).
Xi et al., "Palladim(II)-Catalyzed Oxidative-C-H/C-H Cross Coupling of Heteroarenes", *Journal of the American Chemical Society*, 132: 1822-1824 (2010).
Morita et al., "Triple-Stranded Metall0-Helicates Addressable as Lloyd's Electron Spin Qubits", *Journal of the American Chemical Society*, 132(20): 6944-6946 (2010).
Ra et al., "90 -Bridging 1,3-heterocyclic aromatic rings and the first hyperpolarizability of nonlinear optical compounds", *Journal of Molecular Structure*, 677(1-3): 173-178(2004).
Guo et al., "A novel-non-destructive readout method for rewritable storage systems of diaryiethene photochromic molecules", *Proceeding of SIPE-The International Society for Optical Engineering*, 4085: 158-161 (2001).
Tang et al., "Organic electroluminescent diodes", *Applied Physics Letters*, 51(12): 913-915 (1987).
Burroughes, et al., "Light-emitting diodes based on conjugated polymers", *Nature*, 347: 539-541 (1990).
International Search Report for International Patent Application No. PCT/AU2011/001344 (mailed Jan. 5, 2012).
Song, et al., "Novel Disubstituted Phenylene-Linked Bis-imidazole Derivatives: Facile Synthesis and Optical Properties", *Helvetica Chimica Acta.* 93: 2397-2405 (2010).
Chemical Abstracts Accession No. 2010:1205795 & CAS Registry File RNs 35345-20-1, 1246439-66-6, 1246439-67-7.
Chemical Abstracts Accession No. 2010:927345 & CAS Registry File RN 21036-73-7, 1245794-35-7, 1245794-40-4, 1245794-41-5, 1245794-42-6, 1245794-43-7, 1245794-46-0, 1245794-48-2, 1245794-49-3.
Chemical Abstracts Accession No. 2009:1617226 & CAS Registry File RN 1241962-21-9.
Extended European Search Report for European Patent Application No. 11833639.5 (mailed Sep. 1, 2014).
Vlasova et al., "Synthesis and Properties of 1-Methyl-2-phenyl-5-(2-furyl)- and 1-Methyl-2phenyl-5-(2-thienyl)imidazoles," *Russian Journal of Applied Chemistry*, 83(6):1027-1031 (2010).

* cited by examiner

ORGANIC ELECTROLUMINESCENT DEVICE

This application is a U.S. National Stage Application under 35 U.S.C. §371 of International Patent Application No. PCT/AU2011/001344 filed 21 Oct. 2011, which claims the benefit of priority to Australian Patent Application No. 2010904715 filed 22 Oct. 2010 and Australian Patent Application No. 2011903758 filed 13 Sep. 2011, the disclosures of all or which are incorporated by reference herein in their entireties. The International Application was published in English on 26 Apr. 2012 as WO 2012/051667. To the extent appropriate, a claim of priority is made to each of the above disclosed applications.

FIELD OF THE INVENTION AND RELATED ART

The present invention relates to organic electroluminescent devices, which are sometimes otherwise referred to as organic light emitting diodes (OLED). Organic electroluminescent devices emit light on the application of an electric field to one layer or multiple layers of an organic compound (organic material layer). The present invention also relates to organic compounds suitable for use in such devices.

An organic electroluminescent device is generally comprised of a pair of electrodes forming an anode and a cathode, and one layer or multiple layers comprising a hole injection layer, emission layer (with either fluorescent or phosphorescent material) and electron transporting layer. Into the organic layer(s), holes and electrons are injected from the anode and the cathode, respectively, thus resulting in excitons within the emission material. When the excitons transition to ground state, the organic luminescence device emits light.

According to the first study by Eastman Kodak Co. ("Appl. Phys. Lett", vol. 51, pp. 913 (1987), an organic electroluminescent device which comprised a layer of an aluminium quinolinol complex (as electron transporting and luminescent material) and a layer of a triphenylamine derivative (as a hole transporting material) resulted in luminescence of about 1,000 cd/m$^2$ under an application of a voltage of 10 V. Examples of related U.S. patents include U.S. Pat. Nos. 4,539,507; 4,720,432 and 4,885,211.

Further studies by Baldo et al. revealed a promising OLED using phosphorescent material as dopant. The quantum yield of the phosphorescent OLED was significantly improved (U.S. Pat. No. 6,830,828).

In addition to the above-mentioned OLED, polymer organic electroluminescent device (PLED) using a conjugated polymer material has been reported by a group from Cambridge University (Nature, vol. 347, pp. 539-(1990), U.S. Pat. Nos. 5,247,190; 5,514,878 and 5,672,678).

PLED has an advantage in terms of device fabrication as a printing methodology may be adopted for soluble polymer materials.

Although in the past twenty years OLED and PLED have shown significant progress to in their performance, there still remain problems that need to be solved.

For instance, organic electroluminescent devices described above still show insufficient performance in terms of durability when used for a long time. The performance of organic electroluminescent devices can be further improved by studying new materials such as hole injection materials, hole transporting materials, host materials, emission materials and some others. Additionally, improvement of the device fabrication process is required.

An important consideration to improving organic electroluminescent device performance is to further decrease the driving current within the device in order to enhance device lifetimes. For example, some materials that address this concern have been proposed (U.S. Pat. No. 6,436,559, JP 3571977, JP 3614405). Despite these advances in organic electroluminescent devices' using such materials, further improvements regarding stability and the performance are still required.

SUMMARY OF THE INVENTION

A present invention provides improvements to the problems encountered in organic electroluminescent devices as mentioned above, or provides a useful alternative.

Specific embodiments may provide an organic electroluminescent device with high efficiency and longer life time.

Specific embodiments may also provide a stable device which has reduced current leakage at low current range.

According to the invention, there is provided an organic electroluminescent device comprising:
a pair of electrodes comprising an anode and a cathode, and
one or more layers of organic compound arranged between the pair of electrodes,
wherein the organic compound layer, or one or more of the organic compound layers, comprises a compound represented by the following formula (1)

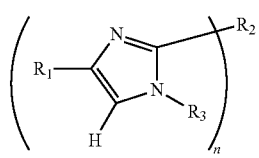

wherein:
$R_1$ to $R_2$, are the same or different and are each independently selected from the group consisting of: substituted or unsubstituted aryl group or substituted or unsubstituted heterocyclic group.

$R_3$ is selected from the group consisting of: substituted or unsubstituted aryl group, substituted or unsubstituted heterocyclic group, substituted or unsubstituted alkyl group or cyano group.

When n=1; $R_1$ or $R_2$ is a substituted or unsubstituted thiophene group.

When n=2; $R_2$=nothing.

One embodiment of the above invention, $R_1$ is a thiophene group. In this embodiment, the invention provides a device, wherein the compound is of formula (1a):

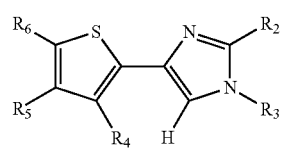

$R_2$ is selected from the group consisting of: substituted or unsubstituted aryl group or a substituted or unsubstituted heterocyclic group.

$R_3$ is selected from the group consisting of: substituted or unsubstituted aryl group or a substituted or unsubstituted heterocyclic group, substituted or unsubstituted alkyl group or a hydrogen atom $R_4$ to $R_6$ are the same or different, and are each independently selected from the is group consisting of hydrogen atom, halogen atom, nitro group, ketone group, amide group, cyano group, carboxylate group, sulfonate group, substituted or unsubstituted aryl group, substituted or unsubstituted alkyl group and substituted or unsubstituted heterocyclic group, or are pairs of substituents in which $R_4$ and $R_5$, or $R_5$ and $R_6$ together form a substituted or unsubstituted cyclic group.

In another embodiment of the above invention, the $R_2$ group of formula (1) is a thiophene group. In this embodiment, the invention provides a device, wherein the compound is of formula (1b):

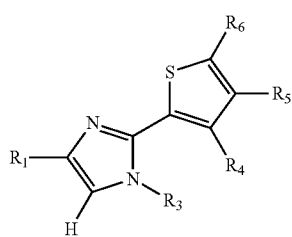

1b $R_1$ is selected from the group consisting of: substituted or unsubstituted aryl group or a substituted or unsubstituted heterocyclic group.

$R_3$ is selected from the group consisting of: substituted or unsubstituted aryl group or a substituted or unsubstituted heterocyclic group, substituted or unsubstituted alkyl group or a hydrogen atom.

$R_4$ to $R_6$ are the same or different, and are each independently selected from the group consisting of hydrogen atom, halogen atom, nitro group, ketone group, amide group, cyano group, carboxylate group, sulfonate group, substituted or unsubstituted aryl group, substituted or unsubstituted alkyl group and substituted or unsubstituted heterocyclic group, or pairs of substituents in which $R_4$ and $R_5$, or $R_5$ and $R_6$ together form a substituted or unsubstituted cyclic group.

In a further embodiment of the above invention, the $R_2$ group of formula (1) is an imidazole group. In this embodiment the invention provides a device, wherein the compound is of formula (1c):

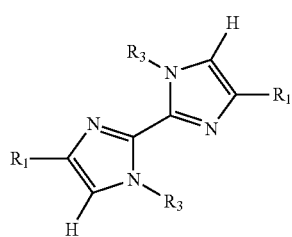

1c $R_1$ is selected from the group consisting of: substituted or unsubstituted aryl group or a substituted or unsubstituted heterocyclic group.

$R_3$ is selected from the group consisting of: substituted or unsubstituted aryl group or a substituted or unsubstituted heterocyclic group, substituted or unsubstituted alkyl group.

In another aspect of the invention, there is provided a compound for use in an electroluminescent device represented by the following formula (1)

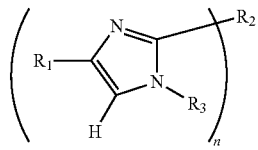

1 wherein:

$R_1$ to $R_2$, are the same or different and are each independently selected from the group consisting of: substituted or unsubstituted aryl group or substituted or unsubstituted heterocyclic group.

$R_3$ is selected from the group consisting of: substituted or unsubstituted aryl group, substituted or unsubstituted heterocyclic group, substituted or unsubstituted alkyl group or cyano group.

When n=1; $R_1$ or $R_2$ is a substituted or unsubstituted thiophene group. When n=2; $R_2$=nothing.

In one embodiment of the above invention, the $R_1$ group of formula (1) is a thiophene group. In this embodiment, the invention provides a compound for use in an electroluminescent device of formula (1a):

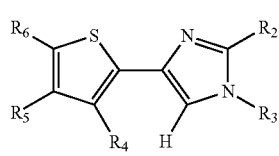

1a $R_2$ is selected from the group consisting of: substituted or unsubstituted aryl group or a substituted or unsubstituted heterocyclic group.

$R_3$ is selected from the group consisting of: substituted or unsubstituted aryl group or a substituted or unsubstituted heterocyclic group, substituted or unsubstituted alkyl group or a hydrogen atom $R_4$ to $R_6$ are the same or different, and are each independently selected from the group consisting of hydrogen atom, halogen atom, nitro group, ketone group, amide group, cyano group, carboxylate group, sulfonate group, substituted or unsubstituted aryl group, substituted or unsubstituted alkyl group and substituted or unsubstituted heterocyclic group, or are pairs of substituents in which $R_4$ and $R_5$, or $R_5$ and $R_6$ together form a substituted or unsubstituted cyclic group.

Another embodiment of the above invention, the $R_2$ group of formula (1) is a thiophene group. In this embodiment, the invention provides a compound for use in an electroluminescent device of formula (1b):

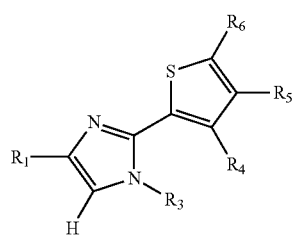

1b $R_1$ is selected from the group consisting of: substituted or unsubstituted aryl group or a substituted or unsubstituted heterocyclic group.

$R_3$ is selected from the group consisting of: substituted or unsubstituted aryl group or a substituted or unsubstituted heterocyclic group, substituted or unsubstituted alkyl group or a hydrogen atom.

$R_4$ to $R_6$ are the same or different, and are each independently selected from the group consisting of hydrogen atom, halogen atom, nitro group, ketone group, amide group, cyano group, carboxylate group, sulfonate group, substituted or unsubstituted aryl group, substituted or unsubstituted alkyl group and substituted or unsubstituted heterocyclic group, or pairs of substituents in which $R_4$ and $R_5$, or $R_5$ and $R_6$ together form a substituted or unsubstituted cyclic group.

A further embodiment of the above invention, $R_2$ is an imidazole group. In this embodiment the invention provides a compound for use in an electroluminescent device of formula (1c):

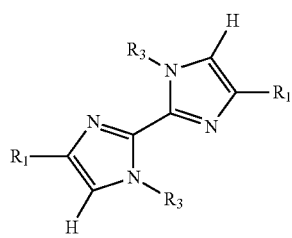

1c $R_1$ is selected from the group consisting of: substituted or unsubstituted aryl group or a substituted or unsubstituted heterocyclic group.

$R_3$ is selected from the group consisting of: substituted or unsubstituted aryl group or a substituted or unsubstituted heterocyclic group, substituted or unsubstituted alkyl group.

In a further aspect the invention provides for use of the compound represented by formulae (1), (1a), (1b), (1c) above in an electroluminescent device.

In a preferred form of the above embodiments, $R_3$ is selected from the group of a hydrogen atom, a substituted or unsubstituted alkyl group, a substituted or unsubstituted monocyclic or polycyclic aromatic compound with 2 or more sites for attachment and a substituted or unsubstituted monoheterocyclic or polyheterocyclic compound with 2 or more sites for attachment.

When $R_1$ to $R_3$ is an aryl group, it may be monocyclic or polycyclic.

As mentioned above, $R_1$ to $R_6$ may be each independently selected from substituted or unsubstituted heterocyclic groups. The heterocyclic groups may be polyheterocyclic.

Figure 1:
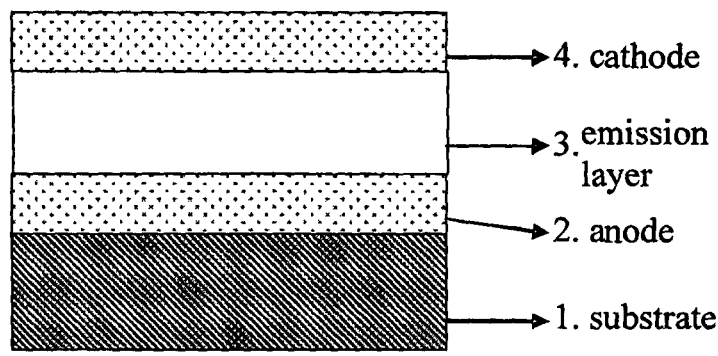
FIG. 1 is a schematic illustration of the basic structure of an organic electroluminescent device according to an embodiment of the invention.

Table 1 is a summary of device properties based on two selected materials 53 and 5, and one commercial material (NPD) for the reference purpose.

DETAILED DESCRIPTION OF THE PREFERRED EMBODIMENTS

The organic electroluminescent device according to the present invention is composed of organic compounds layer(s) aligned between an anode and a cathode.

The organic layer(s) may be constituted by:
a single layer doped with a compound of formula (1), or
multiple layers of which at least one layer may be doped with a compound of formula (1), or at least one layer is a layer comprised of a compound of formula (1) doped with a separate dopant, or
multiple layers of which at least one layer may be comprised entirely of a compound of formula (1).

The term "compound" is used in its broadest sense to refer to any chemical substance of formula (1), and includes polymers, monomers and the like. It will be understood that some forms of the compound of formula (1) are polymer forms.

Formula (1)

The compounds of formula (1) have an imidazole ring structure. $R_1$ to $R_2$, are the same or different and are each independently selected from the group consisting of: substituted or unsubstituted aryl group or substituted or unsubstituted heterocyclic group.

$R_3$ is selected from the group consisting of: substituted or unsubstituted aryl group, substituted or unsubstituted heterocyclic group, substituted or unsubstituted alkyl group or cyano group.

When n=1; $R_1$ or $R_2$ is a substituted or unsubstituted thiophene group.

When n=2; $R_2$=nothing.

Specific embodiments of the compounds of the invention will have a melting point greater than 100° C. and a glass transition temperature greater than 100° C. It is also expected that the band gap for the compounds will be between 2.5 to 3.5 eV.

The term "aryl" is well understood in the art of chemistry, and is used to refer to any aromatic substituent. The aromatic substituent preferably contains one or more rings, such as from one to four fused aromatic rings, and between 5 and 50 ring atoms. Aromatic substituents contain a set of covalently-bound atoms with: a delocalized conjugated π system, most commonly an arrangement of alternating single and double bonds; a coplanar structure, with all the contributing atoms in the same plane; atoms of the system arranged in one or more rings, and an even number of π delocalized electrons, but not a multiple of 4 π electrons (thus 4n+2 π electrons, where n=0 or a positive integer).

Any aromatic groups conforming to this rule are within the definition of aryl. The aryl group may be carbocyclic (i.e. contain carbon and hydrogen only) or may be heteroaromatic (i.e. contain carbon, hydrogen, and at least one heteroatom). The aryl group may be monocyclic such as a phenyl, or a polycyclic aryl group such as naphthyl or anthryl. Examples of aryl groups include a phenyl group, biphenyl group, terphenyl group, naphthyl group, anthryl group, pyrenyl group, etc.

The term "heterocyclic", and similarly "heterocyclic group" or "heterocyclic ring" is well understood in the art of organic chemistry, and is used to refer to any cyclic groups containing one or more rings, such as between one and four rings, and between 5 to 50 (preferably 5 to 20) ring atoms, of which at least one atom is a heteroatom. The heteroatoms may be selected from one or more of O, N, S and Si. The heterocyclic group for the formula (1) may be a 5 or 6 membered heterocyclic ring comprising carbon atoms with one or more of any of the following atoms: nitrogen, oxygen, sulphur and silicon, such as pyrrolyl, thienyl, pyridyl or pyridazinyl. The heterocyclic group may comprise a single heterocyclic ring, or more than one linked or fused rings, with at least one ring containing a heteroatom. One subclass of heterocyclic groups are the heteroaromatic (or heteroaryl) groups, which are aromatic groups containing one or more heteroatoms selected from one or more of O, N and S. Such heteroaromatic groups also fall within the definition of aryl group. Some specific examples for heterocyclic groups are pyrrole, triazole, imidazole, pyrazole, 1,2,5-oxathiazole, isoxazole, oxazole, furan, pyran, pyrone, thiazole, isothiazole, pyrrolidine, pyrroline, imidazolidine, pyrazolidine. Other examples include moieties of benzimidazole, thiophene, benzothiophene, oxadiazoline, indoline, carbazole, pyridine, quinoline, isoquinoline, benzoquinone, pyrazoline, imidazolidine, piperidine, etc The heterocyclic group may be monocyclic or polycyclic. According to some embodiments, the heterocyclic group is polycyclic. An example of a polycyclic heterocyclic group within this class is carbazole.

In formula (1), $R_3$ may be an alkyl group, which may be unsubstituted, or substituted by a suitable substituent. The alkyl group for the formula (1) may be a linear or branched alkyl group or cyclic alkyl group, comprising of between (and including) 1 and 20 carbon atoms. Examples of linear alkyl groups include methyl, propyl or decyl, and examples of branched alkyl groups include iso-butyl, tert-butyl or 3-methyl-hexyl. Examples of cyclic alkyl groups include mono cyclohexyl and fused alkyl cyclic ring systems.

In formula (1), the aryl or alkyl or heterocyclic group may additionally have one or more substituents selected from any suitable substituents known in the art. Suitable substituents may be selected from the group consisting of: halogen atom, nitro group, ketone group, amide group, cyano group, carboxylate group, sulfonate group, alkoxy group, aryloxy group, amino group, alkylamino group, arylamino group, another aryl, alkyl or heterocyclic group, in which each of the aryl, alkyl or heterocyclic groups may be further substituted by one or more further substituents. Thus, the further substituents on the aryl, alkyl or heterocyclic group substituents may be selected from one or more of a halogen atom, nitro group, ketone group, amide group, cyano group, carboxylate group, sulfonate group, alkoxy group, aryloxy group, amino group, alkylamino group and arylamino group.

The substituents may be linked to the aryl, alkyl or heterocyclic group directly by one atom or fused by more than one atom or via a heteroatom such as nitrogen, oxygen, sulphur and silicon. In some cases the substituent may be linked by two or more points of attachment, as in the case of a divalent alkyl group, or an ethylenedioxy group (i.e. —O—CH$_2$CH$_2$—O—).

The term "halogen" or halo refers to fluorine, chlorine, bromine, etc. Nitro refers to —NO$_2$. Ketone refers to compounds containing the group —C(=O)-alkyl or —C(=O)-aryl, where alkyl and aryl are as defined previously. Acetyl (—C(=O)—CH$_3$ is one specific example.

The term amide refers to substituents containing the group —C(O)NR'R", wherein R and R" are selected from H, alkyl, aryl or alkyl-aryl groups, which have been defined previously. The term "imide" refers to substituents containing the group —C(O)NR'C(O)R", wherein R and R" are selected from H, alkyl, aryl or alkyl-aryl groups. The term "imine" refers to substituents containing the group —C(=NR')R", wherein R and R" are selected from H, alkyl, aryl or alkyl-aryl groups. The term "amidine" refers to substituents containing the group —C(=NR')NR"R", wherein R', R" and R⁻ are selected from H, alkyl, aryl or alkyl-aryl groups.

Cyano refers to —C≡N. Hydroxyl refers to —OH. Carboxylate refers to the carboxylate anion —CO$_2$R—, and encompasses carboxylic acids, esters and salts thereof. Sulfonate group refers to sulfonic acids, esters and salts thereof. Alkoxy refers to the group —O-alkyl, where alkyl is as defined previously. Aryloxy refers to the group —O-aryl, where aryl is as defined previously.

The term "amino" refers to the amino group —NH$_2$. The term alkylamino refers to secondary and tertiary alkylamino groups containing one or two alkyl groups on the nitrogen atom. Examples of an "alkylamino group" include dimethylamino group, diethylamino group, dihexylamino group, etc. The term arylamino refers to secondary and tertiary arylamino groups containing one or two aryl groups on the nitrogen atom. Examples of an "arylamino group" include a diphenylamino group, ditolylamino group, isopropyldiphenylamino group, t-butyldiphenylamino group, diisopropyldiphenylamino group, di-t-butyldiphenylamino group, dinaphthylamino group, naphthylphenylamino group, etc.

In formula (1), one or more of $R_1$ to $R_3$ may be a cyano group. Cyano refers to —C≡N.

Formula (1a)

In formula (1a), the $R_1$ of formula (1) is a thiophene group. The term "thiophene" is well understood in the art of organic chemistry. A thiophene group is a 5 member unsaturated heterocyclic ring including a sulphur atom in the ring.

$R_2$ is selected from the group consisting of: substituted or unsubstituted aryl group or a substituted or unsubstituted heterocyclic group.

$R_3$ is selected from the group consisting of: substituted or unsubstituted aryl group or a substituted or unsubstituted heterocyclic group, substituted or unsubstituted alkyl group or a hydrogen atom $R_4$ to $R_6$ are the same or different, and are each independently selected from the group consisting of hydrogen atom, halogen atom, nitro group, ketone group, amide group, cyano group, carboxylate group, sulfonate group, substituted or unsubstituted aryl group, substituted or unsubstituted alkyl group and substituted or unsubstituted heterocyclic group, or are pairs of substituents in which $R_4$ and $R_5$, or $R_5$ and $R_6$ together form a substituted or unsubstituted cyclic group.

The terms aryl group, heterocyclic group, alkyl group, hydrogen atom, halogen atom, nitro group, ketone group, amide group, cyano group, carboxylate group, sulfonate group have been defined above in the context of Formula (1), and those definitions apply equally here.

The optional substituents on the alkyl, aryl and heterocyclic groups are the same as those described above for formula (1), and include halogen atom, nitro group, ketone group, amide group, cyano group, carboxylate group, sulfonate group, alkoxy group, aryloxy group, amino group, alkylamino group, arylamino group, a monomer or polymer chain and another aryl, alkyl or heterocyclic group, in which each of the aryl, alkyl or heterocyclic groups may be further substituted by one or more further substituents. Again, the further substituents on the aryl, alkyl or heterocyclic group substituents may be selected from one or more of a halogen atom, nitro group, ketone group, amide group, cyano group, carboxylate group, sulfonate group, alkoxy group, aryloxy group, amino group, alkylamino group and arylamino group.

The substituents may be linked to the aryl, alkyl or heterocyclic group directly by one atom or fused by more than one atom or via a heteroatom. In some cases the substituent may be linked by two or more points of attachment, as in the case of a divalent alkyl group, or an ethylenedioxy group (i.e. —O—CH$_2$CH$_2$—O—).

In another embodiment, pairs of substituents R$_4$ and R$_5$, or R$_5$ and R$_6$ together form a substituted or unsubstituted cyclic group, The term "cyclic group" is used in its broadest sense to refer to cyclic rings and linked or fused ring systems, which may be carbocyclic or heterocyclic, and may be aliphatic, aromatic, saturated or unsaturated. The ring may be carbocyclic groups (in which all of the ring atoms are carbon atoms, such as cyclohexyl), heterocyclic groups (as described previously), and aromatic or aryl groups (which may be carbon-based aromatic groups or heteroaromatic groups). The cyclic group may contain a single ring, or up to 3 linked or fused rings.

Formula 1b

In formula (1b), R$_2$ of formula (1) is a thiophene group.

R$_1$ is selected from the group consisting of: substituted or unsubstituted aryl group or a substituted or unsubstituted heterocyclic group.

R$_3$ is selected from the group consisting of: substituted or unsubstituted aryl group or a substituted or unsubstituted heterocyclic group, substituted or unsubstituted alkyl group or a hydrogen atom.

R$_4$ to R$_6$ are the same or different, and are each independently selected from the group consisting of hydrogen atom, halogen atom, nitro group, ketone group, amide group, cyano group, carboxylate group, sulfonate group, substituted or unsubstituted aryl group, substituted or unsubstituted alkyl group and substituted or unsubstituted heterocyclic group, or pairs of substituents in which R$_4$ and R$_5$, or R$_5$ and R$_6$ together form a substituted or unsubstituted cyclic group.

The terms aryl group, heterocyclic group, alkyl group, hydrogen atom, halogen atom, nitro group, ketone group, amide group, cyano group, carboxylate group, sulfonate group have been defined above in the context of Formula (1), and those definitions apply equally here.

The optional substituents on the alkyl, aryl and heterocyclic groups are the same as those described above for formula (1), and include halogen atom, nitro group, ketone group, amide group, cyano group, carboxylate group, sulfonate group, alkoxy group, aryloxy group, amino group, alkylamino group, arylamino group, a monomer or polymer chain and another aryl, alkyl or heterocyclic group, in which each of the aryl, alkyl or heterocyclic groups may be further substituted by one or more further substituents. Again, the further substituents on the aryl, alkyl or heterocyclic group substituents may be selected from one or more of a halogen atom, nitro group, ketone group, amide group, cyano group, carboxylate group, sulfonate group, alkoxy group, aryloxy group, amino group, alkylamino group and arylamino group.

The substituents may be linked to the aryl, alkyl or heterocyclic group directly by one atom or fused by more than one atom or via a heteroatom. In some cases the substituent may be linked by two or more points of attachment, as in the case of a divalent alkyl group, or an ethylenedioxy group (i.e. —O—CH$_2$CH$_2$—O—).

In another embodiment, pairs of substituents R$_4$ and R$_5$, or R$_5$ and R$_6$ together form a substituted or unsubstituted cyclic group, The term "cyclic group" is used in its broadest sense to refer to cyclic rings and linked or fused ring systems, which may be carbocyclic or heterocyclic, and may be aliphatic, aromatic, saturated or unsaturated. The ring may be carbocyclic groups (in which all of the ring atoms are carbon atoms, such as cyclohexyl), heterocyclic groups (as described previously), and aromatic or aryl groups (which may be carbon-based aromatic groups or heteroaromatic groups). The cyclic group may contain a single ring, or up to 3 linked or fused rings.

Formula (1c)

In formula (1c), the R$_2$ group in formula (1) is an imidazole group:

R$_1$ is selected from the group consisting of: substituted or unsubstituted aryl group or a substituted or unsubstituted heterocyclic group.

R$_3$ is selected from the group consisting of: substituted or unsubstituted aryl group or a substituted or unsubstituted heterocyclic group, substituted or unsubstituted alkyl group or a hydrogen atom.

The optional substituents on the alkyl, aryl and heterocyclic groups are the same as those described above for formula (1), and include halogen atom, nitro group, ketone group, amide group, cyano group, carboxylate group, sulfonate group, alkoxy group, aryloxy group, amino group, alkylamino group, arylamino group, a monomer or polymer chain and another aryl, alkyl or heterocyclic group, in which each of the aryl, alkyl or heterocyclic groups may be further substituted by one or more further substituents. Again, the further substituents on the aryl, alkyl or heterocyclic group substituents may be selected from one or more of a halogen atom, nitro group, ketone group, amide group, cyano group, carboxylate group, sulfonate group, alkoxy group, aryloxy group, amino group, alkylamino group and arylamino group.

The substituents may be linked to the aryl, alkyl or heterocyclic group directly by one atom or fused by more than one atom or via a heteroatom. In some cases the substituent may be linked by two or more points of attachment, as in the case of a divalent alkyl group, or an ethylenedioxy group (i.e. —O—CH$_2$CH$_2$—O—).

The terms aryl group, heterocyclic group, alkyl group, hydrogen atom, halogen atom, nitro group, ketone group, amide group, cyano group, carboxylate group, sulfonate group have been defined above in the context of Formula (1), and those definitions apply equally here.

Specific examples of the compound represented as formula (1) may include example compounds No. (2) to (62) shown below but are, however, not restricted to those compounds.

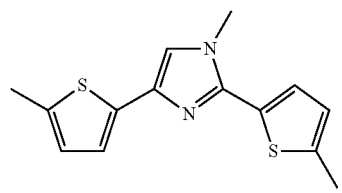

1

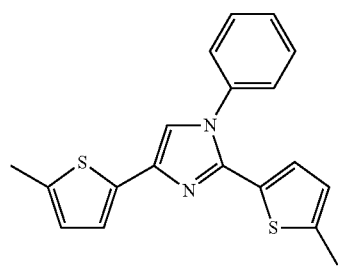

2

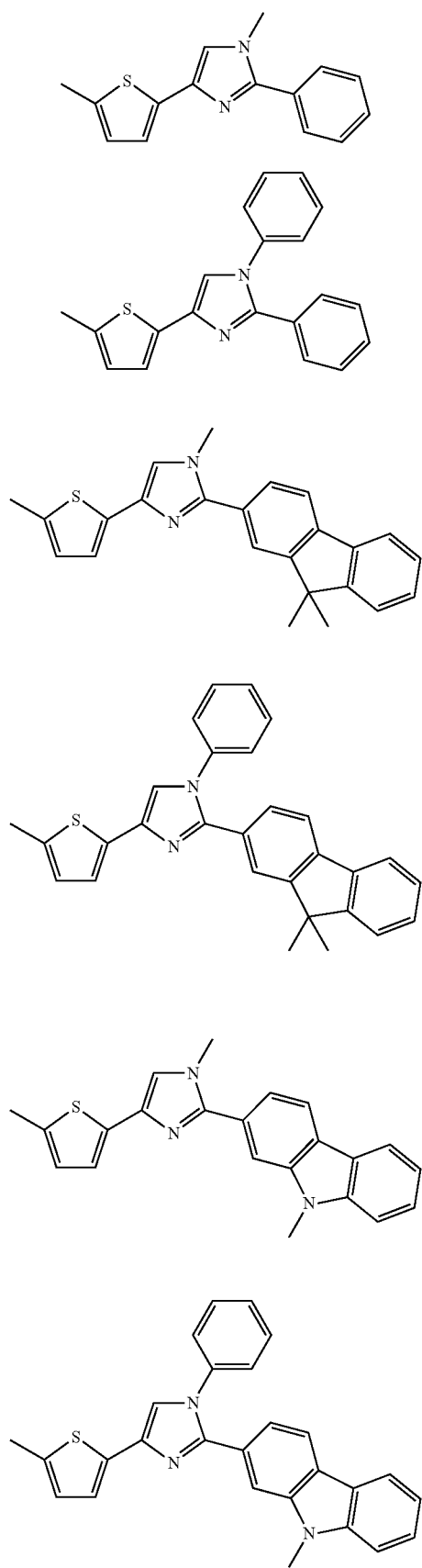
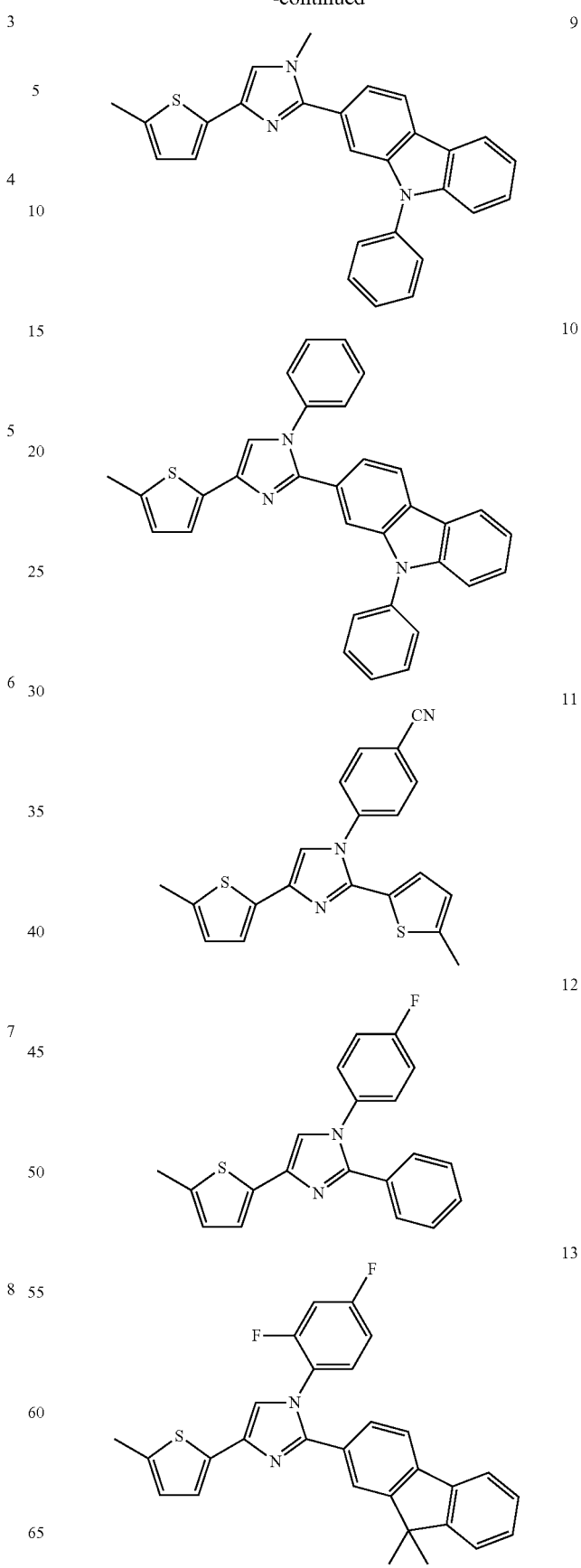

-continued
14
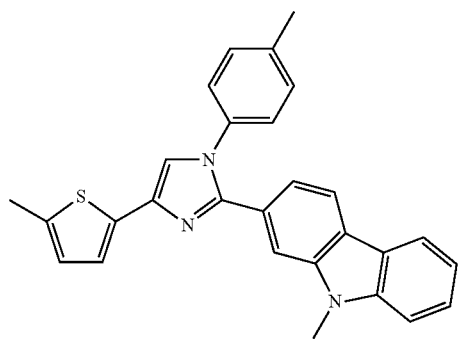
15
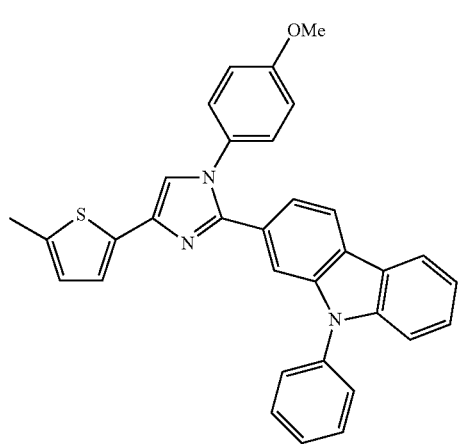
16
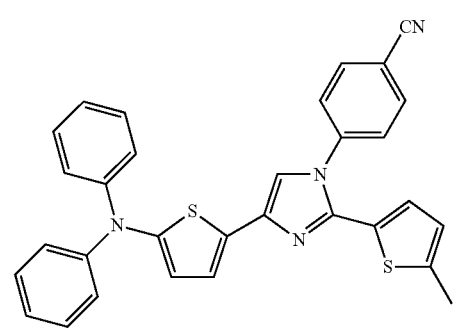
17
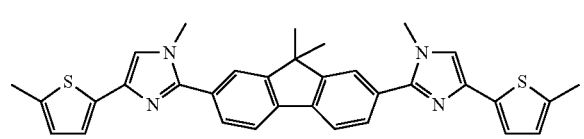
18
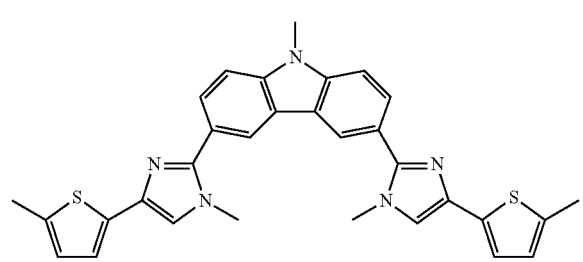
-continued
19
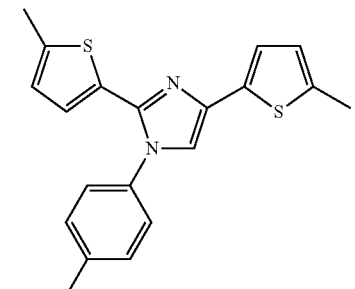
20
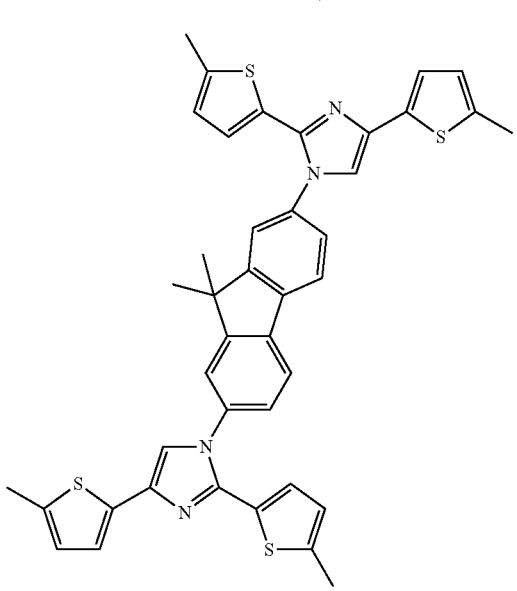
21
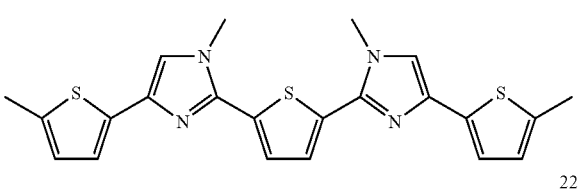
22
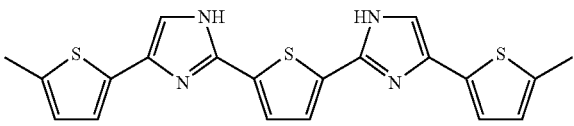
23
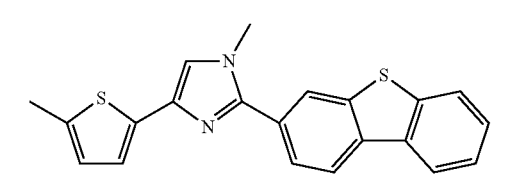

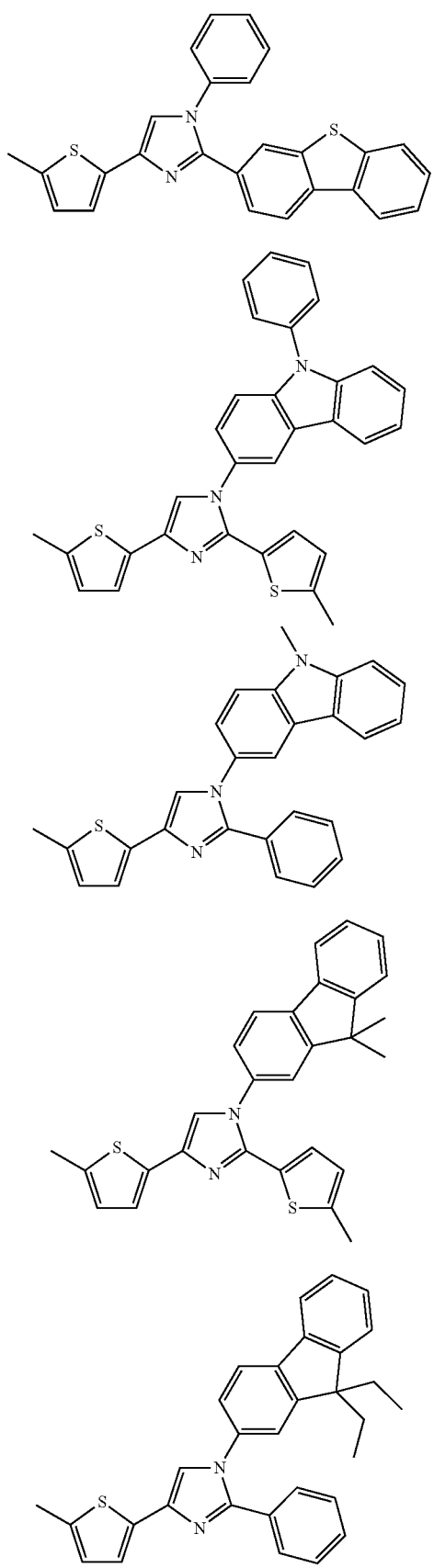
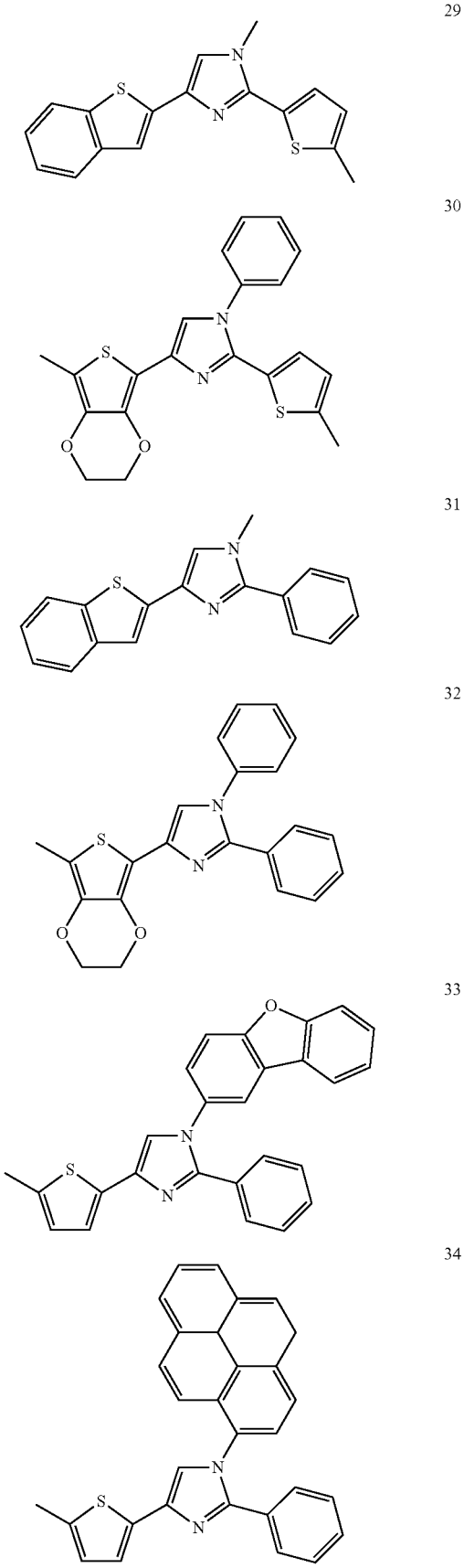

| | |
|---|---|
| 35 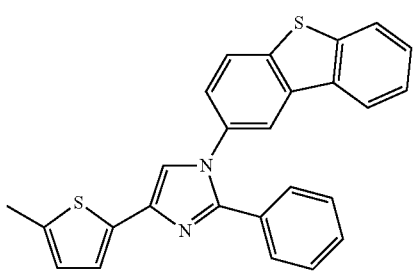 | 41 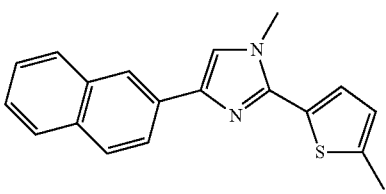 |
| 36 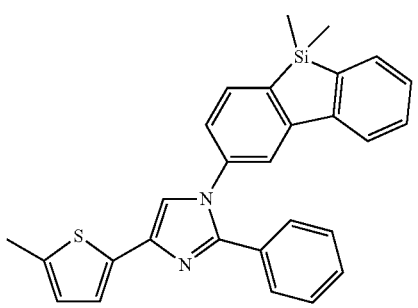 | 42 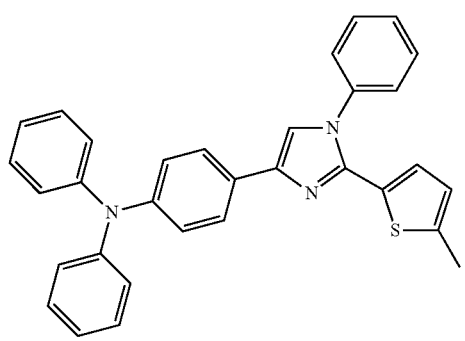 |
| 37 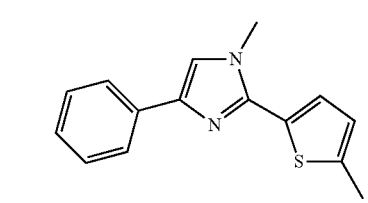 | 43 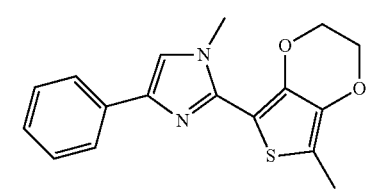 |
| 38 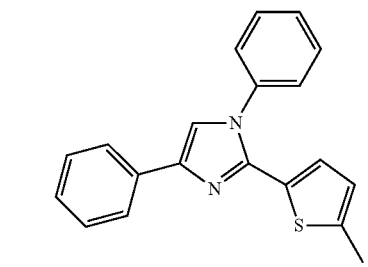 | 44 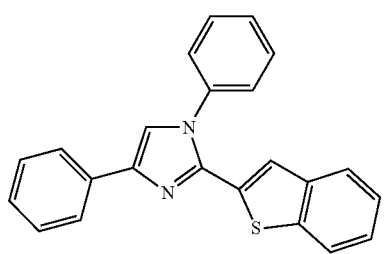 |
| 39 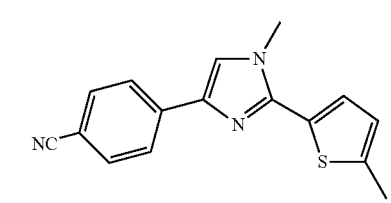 | 45 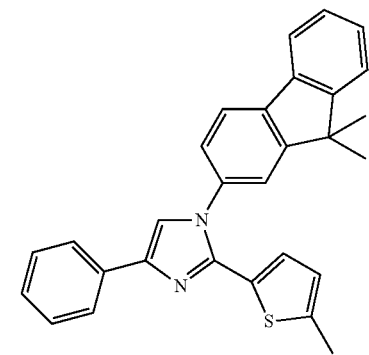 |
| 40 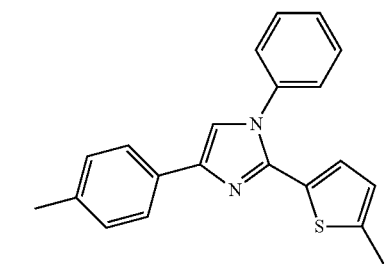 | |

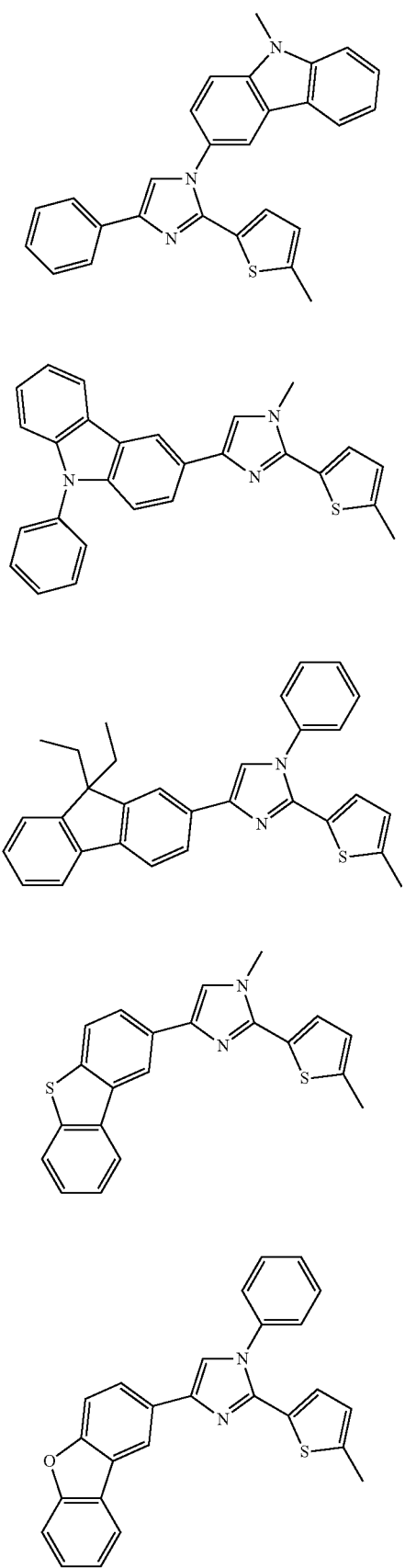
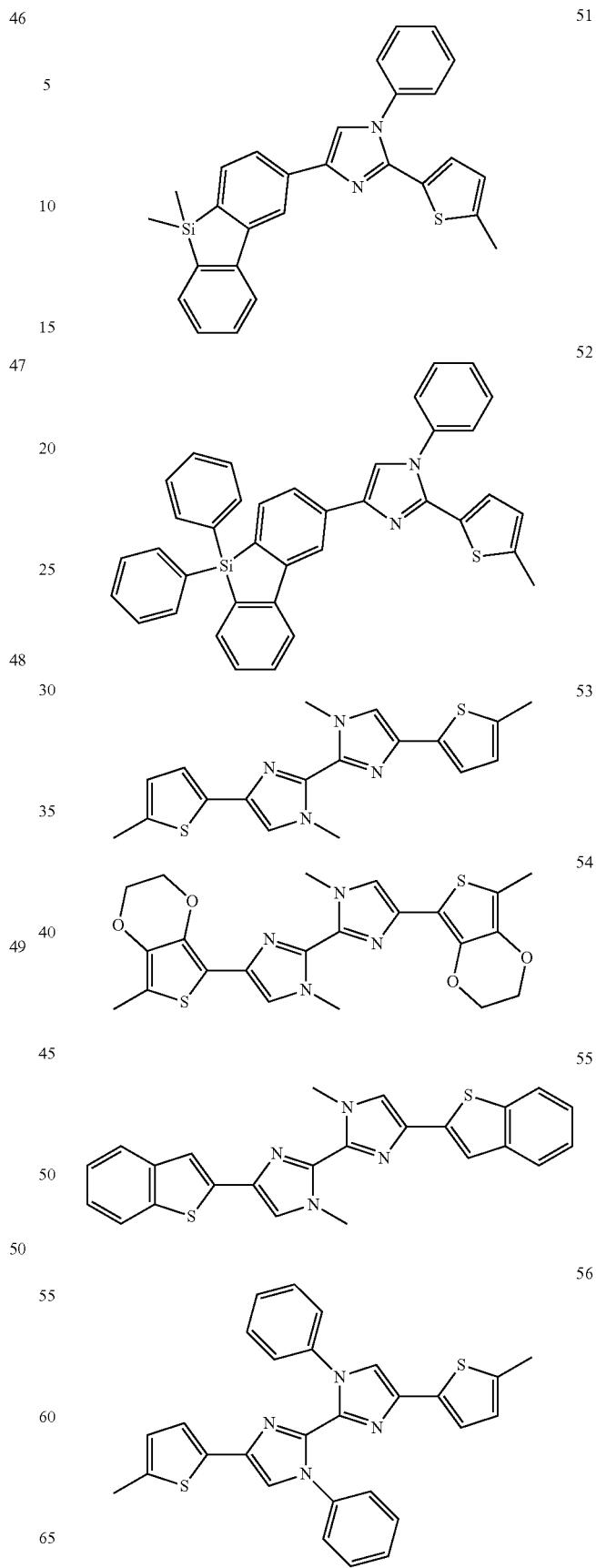

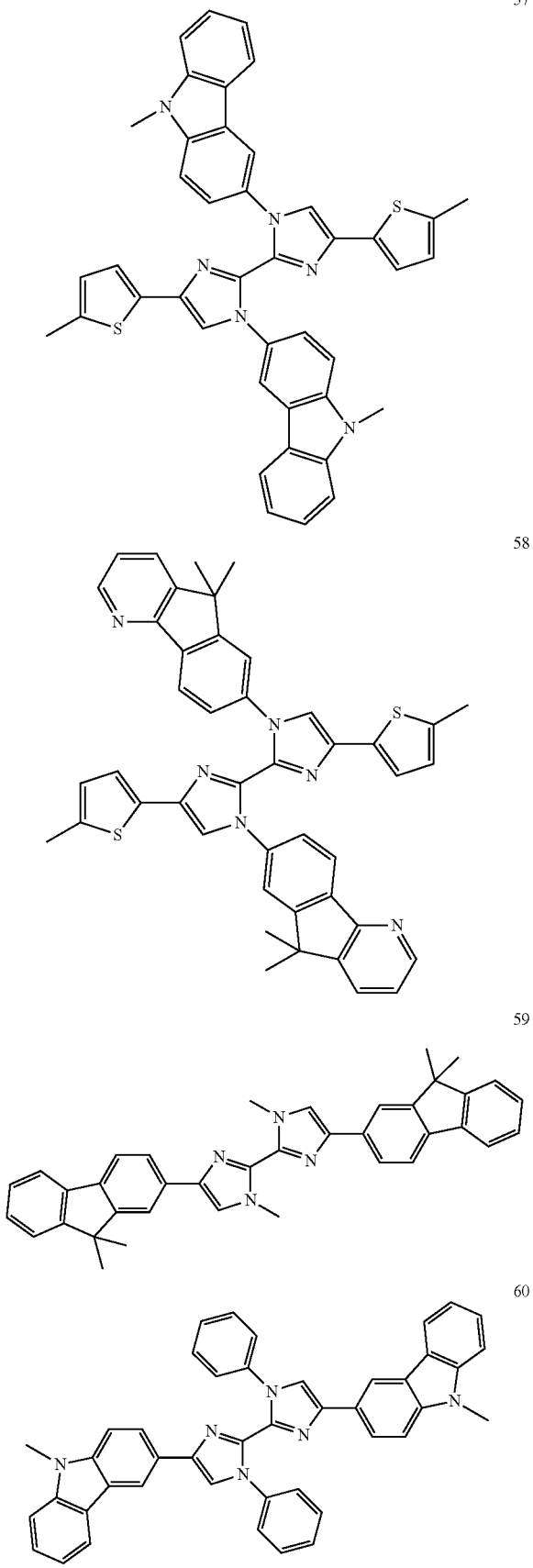

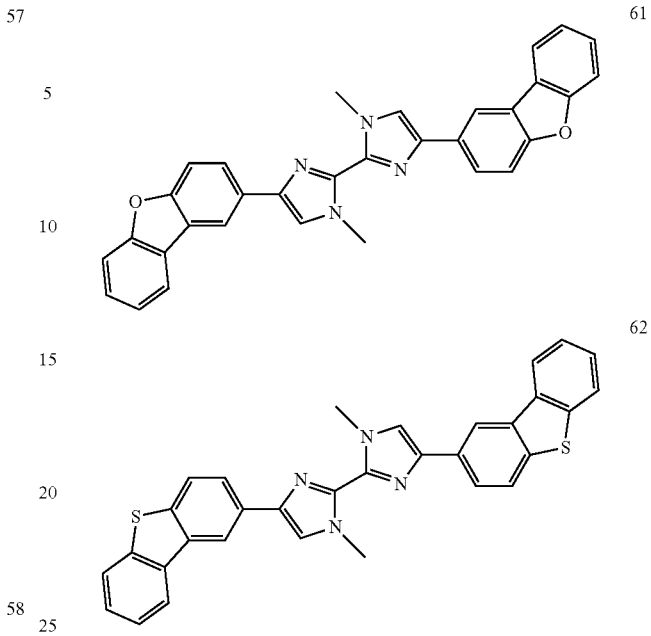

As described above, the organic layer(s) may be constituted by:
a single layer doped with a compound of formula (1), or
multiple layers of which at least one layer may be doped with a compound of formula (1) or at least one layer is a layer comprised of a compound of formula (1) doped with a separate dopant, or
multiple layers of which at least one layer may be comprised entirely of a compound of formula (1).

In the organic luminescence device of the present application, the organic compound layer comprising the above-mentioned compound of the formula (1) may be formed separately, or together, with the other layers (if any other layers are present) between the pair of electrodes (cathode and anode). Suitable formation techniques include vacuum deposition or solution process.

The thickness of the organic compound layer may be preferably less than at most 10 μm, more preferably less than 0.5 μm, even more preferably 0.001-0.5 μm.

Specific embodiments of the invention will now be described in further detail with reference to the accompanying figures, which illustrate a range of possible arrangements for the device of the present invention. It will be understood that these embodiments are provided by way of example only, and are not intended to limit the scope of the invention.

Figure 2:
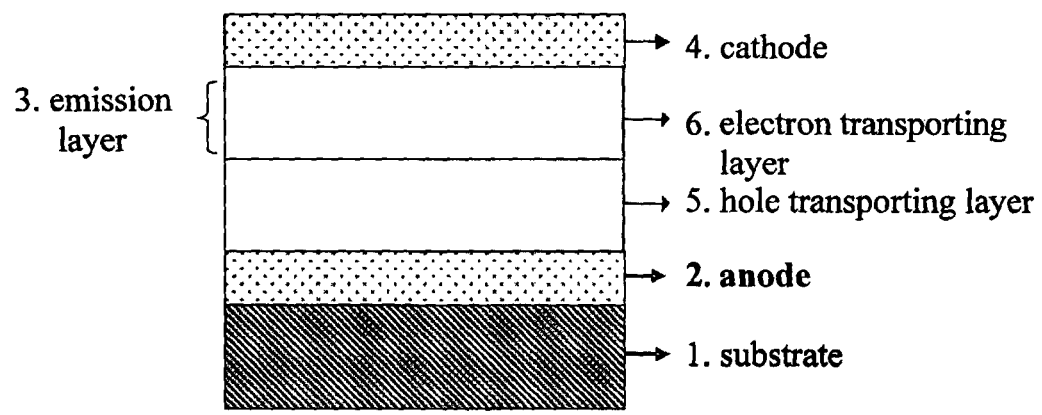
FIG. 2 is a schematic illustration of the basic structure of an organic electroluminescent device according to another embodiment of the invention.
Figure 3:
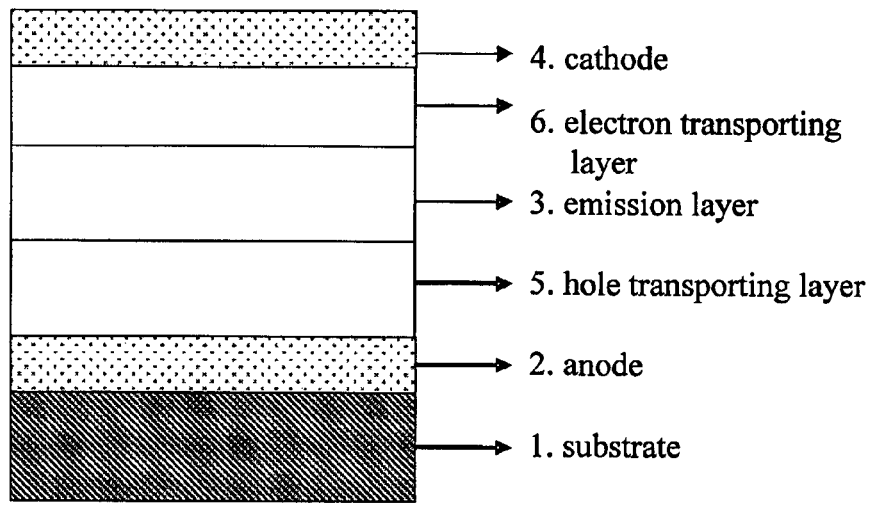
FIG. 3 is a schematic illustration of the basic structure of an organic electroluminescent device according to another embodiment of the invention.

The electroluminescent device of embodiments of the present application may have a single layer structure comprised of only compound as defined by formula (1) as shown in FIG. 1 or be a multiple layered structure of two or more layers as shown in FIGS. 2 and 3.

More specifically, FIG. 1 is a schematic cross section of a first embodiment of the organic electroluminescent device of the present invention. In FIG. 1, the organic electroluminescent device includes a substrate 1, an anode 2 (deposited on the substrate 1), an emission layer 3 (deposited on the anode 2) and a cathode 4 (deposited on the emission layer 3). In this embodiment, the emission layer 3 forms a single organic compound type-layer. This single layer may be composed entirely of a compound having hole transporting ability, electron transporting ability and luminescence ability (associated with the re-combination of electrons and holes) based on its own properties, or through combination with a dopant that enhances the performances of the hole transporting ability, the electron transporting ability and luminescence ability of the host compound. According to some embodiments, the compound of formula (1) can serve as a hole transporting layer with a dopant. According to other embodiments, the compound of formula (1) can function as a dopant. According to other embodiments, the compound of formula (1) can serve as a separate hole injection layer, as described further below.

In FIG. 1, the emission layer 3 may preferably have a thickness of 5 nm to 1 µm, more preferably 5 to 50 nm.

FIG. 2 shows another embodiment of the organic electroluminescent device of the present invention in the form of a multiple layer-type device comprised of a hole transporting layer 5 and an electron transporting layer 6.

Referring to FIG. 2, the organic luminescent device includes a substrate 1, an anode 2 (deposited on the substrate 1), the hole transporting layer 5 (deposited on the anode 2), the electron transporting layer 6 (deposited on the hole transporting layer 5) and a cathode (deposited on the electron transporting layer 6). In this embodiment, either one or both of the hole transporting layer 5 and the electron transporting layer 6 may contain an emissive compound as dopant(s) for forming an emission layer 3. In this case, the hole transporting layer 5 and the electron transporting layer 6 may be comprised of non-luminescent compound(s), respectively. The compound of formula 1 can form the hole transporting layer 5, or a component of the hole transporting layer.

In the embodiment of FIG. 2, each of the hole transporting layer 5 and the electron transporting layer 6 may have the thickness of 5 nm to 1 µm, more preferably 5 nm to 50 nm.

FIG. 3 shows another embodiment of the organic electroluminescent device of the present invention in the form of a multiple layer-type device comprising a hole transporting layer 5, an emission layer 3, an electron transporting layer 6. In FIG. 3, the organic luminescent device includes a substrate 1, an anode 2 (deposited on the substrate 1), the hole transporting layer 5, (deposited on the anode 2), the emission layer 3 (deposited on the hole transporting layer 5), the electron transporting layer 6 (deposited on the emission layer 3) and a cathode (deposited on the electron transporting layer 6). In this embodiment, each of the hole transporting layer, the emission layer and the electron transporting layer may be formed by use of a hole transporting compound, an emissive compound and an electron transporting compound, respectively or as a mixture of these kinds of compounds. The compound of formula 1 can form the hole transporting layer 5, or a component of the hole transporting layer.

Figure 4:
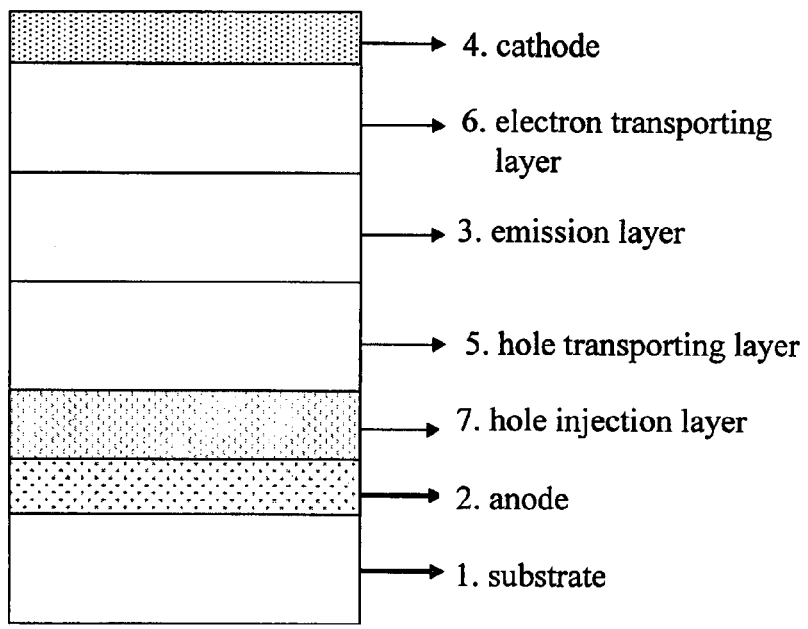
FIG. 4 is a schematic illustration of the basic structure of an organic electroluminescent device according to another embodiment of the invention.

FIG. 4 shows another embodiment of the organic electroluminescent device of the present invention with multiple layers comprising a hole injection layer 7, a hole transporting layer 5, an emission layer 3 and an electron transporting layer 6. In FIG. 4, the organic luminescent device includes a substrate 1, an anode 2 (deposited on the substrate 1), the hole injection layer 7 (deposited on the anode 2), the hole transporting layer 5 (deposited on the hole injection layer), the emission layer 3 (deposited on the hole transporting layer 5), the electron transporting layer 6 (deposited on the emission layer 3) and a cathode (deposited on the electron transporting layer 6). In this embodiment, each of the hole injection layer, the hole transporting layer, the emission layer and the electron transporting layer may be formed by use of a hole injection compound, a hole transporting compound, an emissive compound and an electron transporting compound, respectively or as a mixture of these kinds of compounds. The compound of formula 1 can form the hole injection layer 7 and/or the hole transporting layer 5 (or a component thereof).

In FIGS. 1, 2, 3 and 4, each layer of 3, 5, 6, and 7 may be formed by either vacuum deposition or wet process using low molecule or polymer compound or mixture of low molecule and polymer compound. Each thickness of the layer 3, 5 and 6 may preferably be ranging from 1 nm to 1 µm. Each of the thickness of the cathode and the anode may be preferably 100-200 nm.

The organic layer structures in the devices shown in FIGS. 1, 2, 3 and 4 represent the basic structure, respectively, so that the structure may be appropriately optimized depending on characteristics demanded. Examples of suitable modifications include the incorporation of one or more additional layers.

For example, the hole transporting layer may be altered to comprise a hole injection layer (deposited on the anode) and hole transporting layer (deposited on the hole injection layer).

More specific embodiments of the device structure other than those of FIGS. 1, 2, and 4 are shown below, but not restricted to these device structures.

(1) Anode/hole transporting layer/emission layer/electron transporting layer/electron injection layer/cathode
(2) Anode/hole injection layer/emission layer/electron transporting layer/electron injection layer/cathode
(3) Anode/insulating layer/hole transporting layer/emission layer/electron transporting layer/cathode
(4) Anode/hole transporting layer/emission layer/electron transporting layer/insulating layer/cathode
(5) Anode/inorganic semiconductor/insulator/hole transporting layer/emission layer/insulator/cathode
(6) Anode/insulating layer/hole transporting layer/emission layer/electron transporting layer/insulating layer/cathode
(7) Anode/insulating layer/hole injection layer/hole transporting layer/emission layer/electron transporting layer/electron injection layer/cathode
(8) Anode/insulating layer/hole injection layer/hole transporting layer/emission layer/electron transporting layer/electron injection layer/insulating layer/cathode In the embodiments described above, more preferable device structures are (1), (2), (3), (7) and (8), although this is not a restriction. According to some embodiments, the compound of the formula (1) may be formed as a hole injection layer or a hole generation layer. In this case, the hole injection layer or the hole generation layer has a thickness of 1 nm to 1 µm, more preferably 1-50 nm. According to some embodiments, there is provided the use of the compound of formula (1) as a hole injection material, or a hole generation material, as a hole injection layer or a hole generation layer, or as a dopant in a hole transporting layer.

In some embodiments, the compound of the formula (1) may be used in combination with a hole transporting compound (or material), an electron transporting compound and/or an emission compound, examples of which may include the following.

Hole Transporting Materials/Compounds:
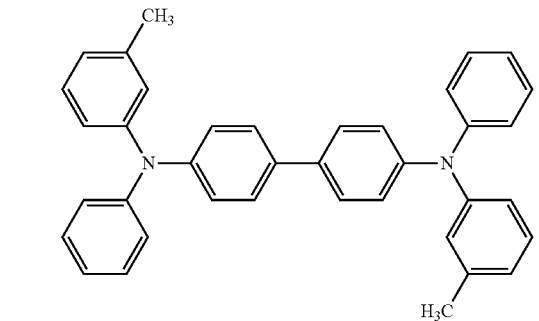
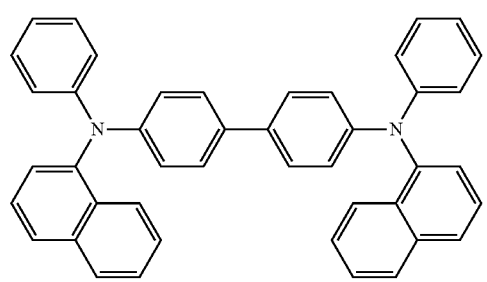
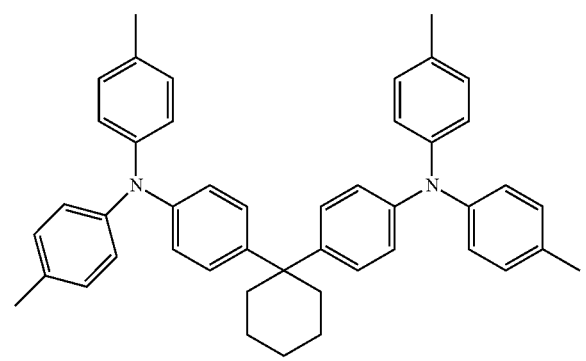
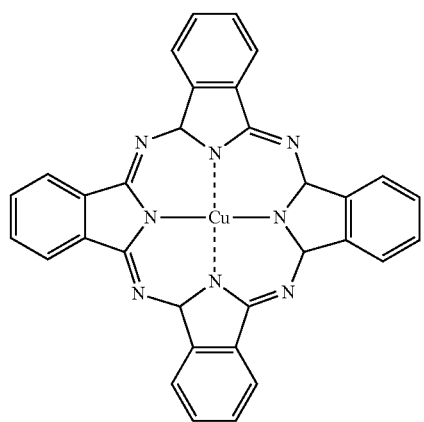
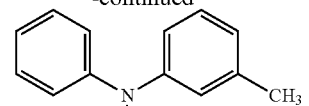
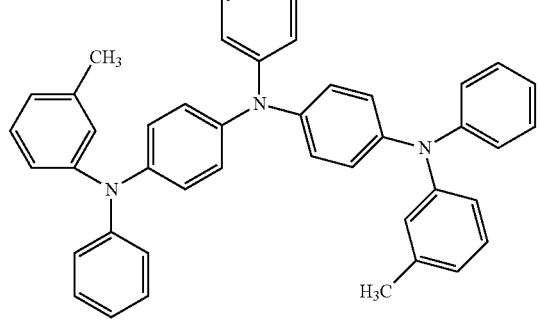
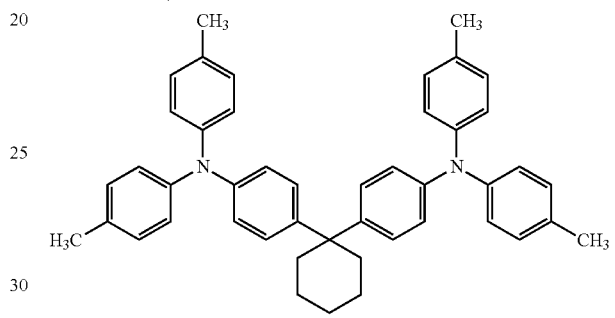
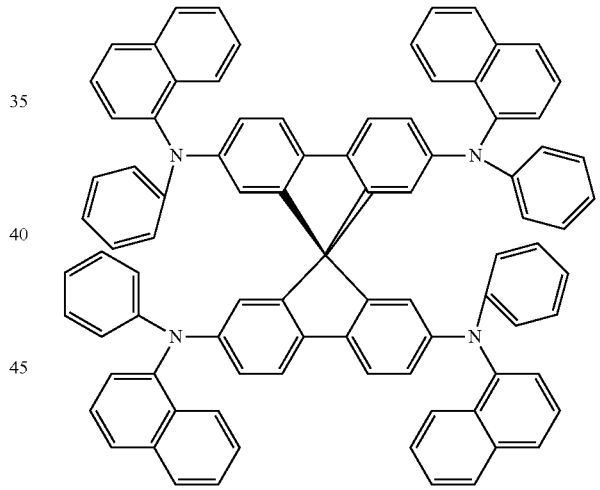
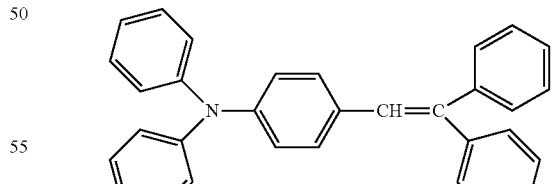
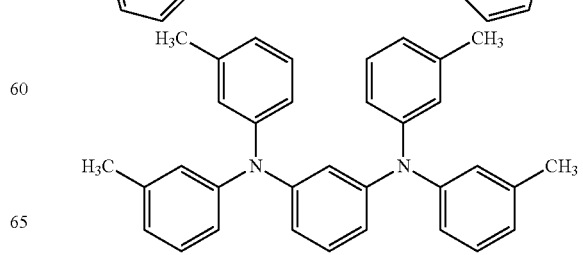

-continued
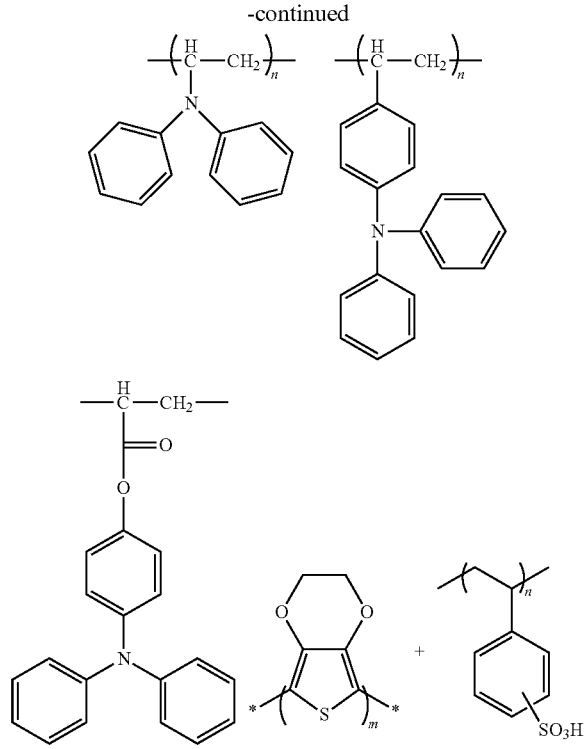
Electron Transporting Materials/Compounds:
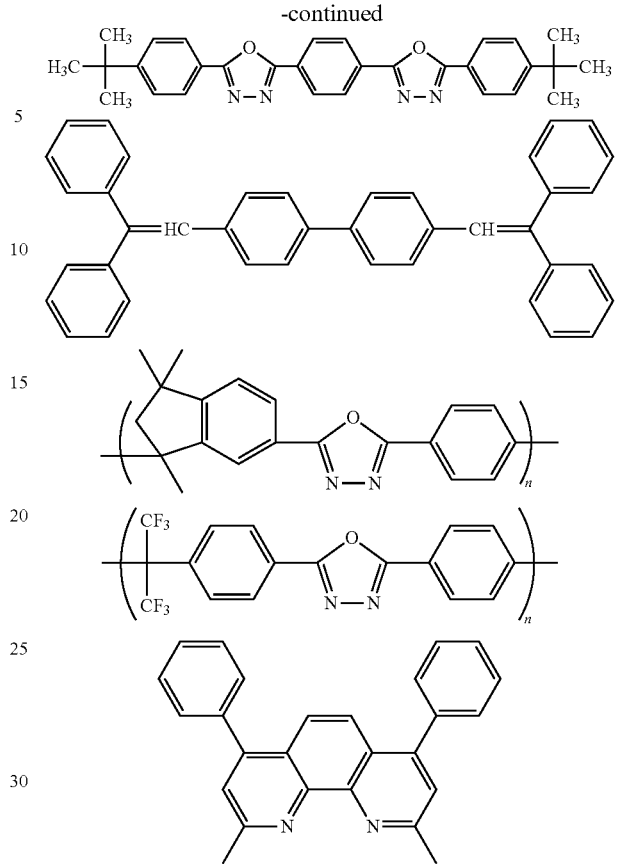
-continued
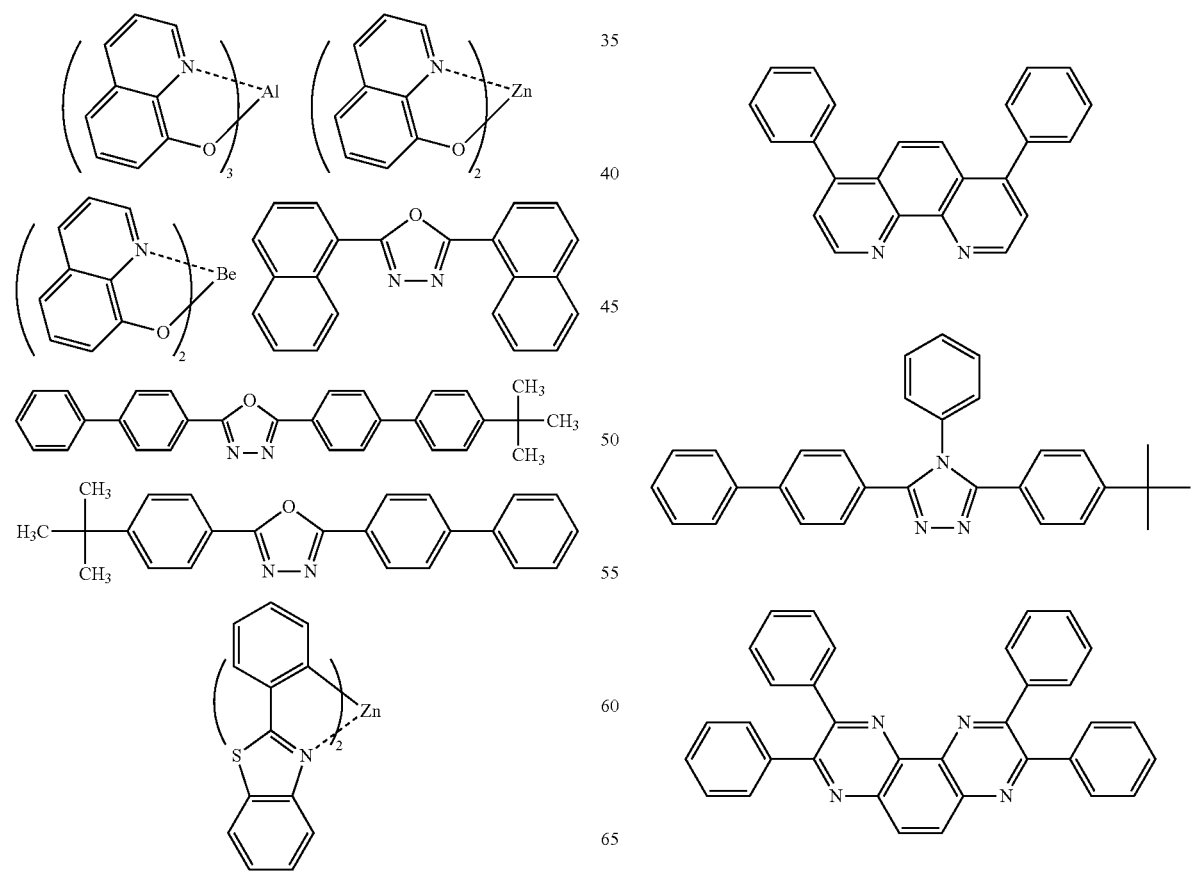

Emission Materials/Compounds:

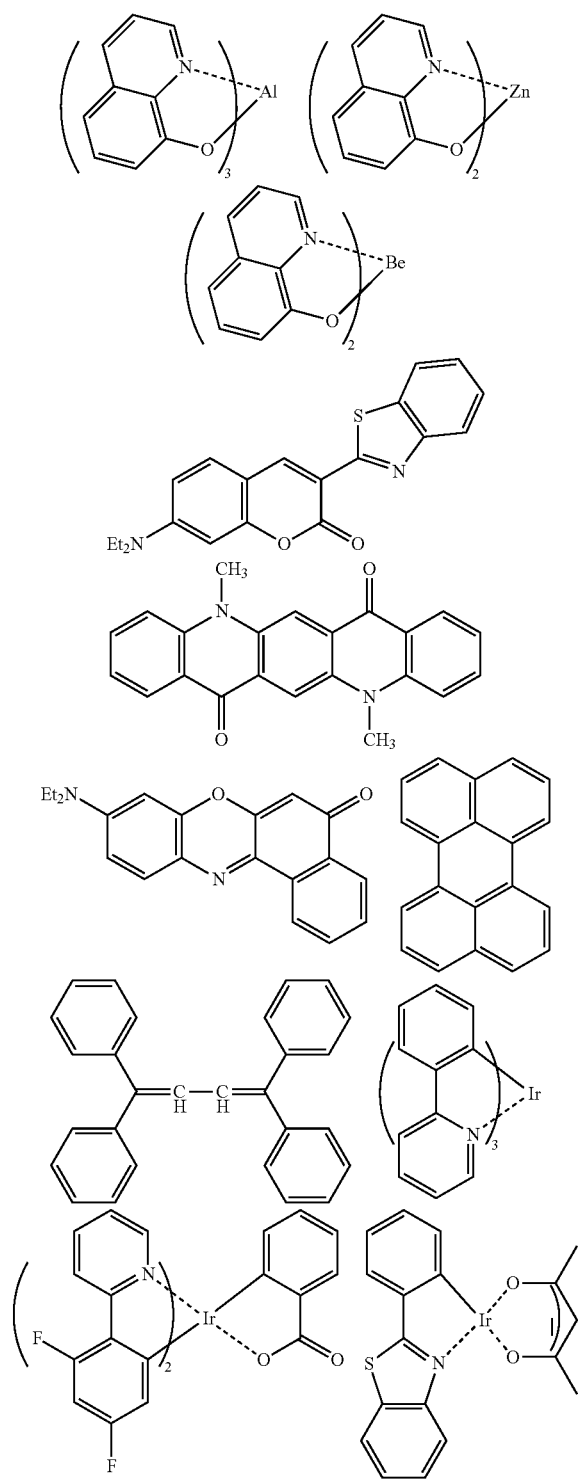

As a material for the anode (e.g. 2 in FIGS. 1-4), it is preferred to use one having a large work function, examples of which may include metals, such as gold, platinum, nickel, palladium, cobalt, selenium, vanadium and their alloys; metal oxides, such as tin oxide, zinc oxide, indium zinc oxide (IZO) and indium tin oxide (ITO) and electroconductive polymers, such as polyaniline, polypyrrole and polythiophene and derivatives thereof. These compounds may be used singly or in combination of two or more species.

As a material for the cathode (e.g. 4 in FIGS. 1-4), it is preferred to use one having a smaller work function, usually under 4.0 eV, examples of which may include; metals such as sodium, magnesium, lithium, potassium, aluminium, indium, silver, lead, chromium and their alloys, or oxides. In the case of metal oxide, those such as indium oxide (ITO), indium zinc oxide (IZO) and zinc oxide are suitable.

The insulating layer may be deposited adjacent to either electrode to avoid current leakage as mentioned in embodiments (3) to (8). As the insulating material, it is preferred to use an inorganic compound, examples of which may include aluminium oxide, lithium fluoride, lithium oxide, caesium oxide, magnesium oxide, magnesium fluoride, calcium oxide, calcium fluoride, aluminium nitride, titanium oxide, silicon oxide, silicon nitride, boron nitride, vanadium oxide.

The substrate (e.g., 1 shown in FIGS. 1 to 4) for the organic electroluminescence device of the present invention may include an opaque substrate made from any suitable material, such as metal or ceramics, or a transparent substrate made from any suitable transparent material such as glass, quartz, plastics, etc. It is possible to form the substrate with a colour filter film, a fluorescent colour conversion film, dielectric reflection film, etc., thus controlling such aspects of the emitted luminescent light.

The devices of the present application can be provided in the form of a stacked organic electroluminescent (EL) device. The present application also extends to electronic devices comprising the organic electroluminescent device of the present invention, including displays and light sources.

The present invention will be described below in detail with preparation examples and the device examples, but the present invention is not intended to be restricted to these examples.

Example 1

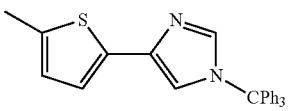

4-(5-Methylthiophen-2-yl)-1-trityl-1H-imidazole 1

A mixture of 4-iodo-1-trityl-1H-imidazole (7.95 g, 18.2 mmol), 5-methylthiophene-2-boronic acid pinacol ester (4.90 g, 21.9 mmol), $Na_2CO_3$ (7.66 g, 73.0 mmol) in $H_2O$ (20 mL) and dioxane (100 mL) was degassed ($N_2$ bubbling). $Pd(PPh_3)_4$ (500 mg) was added and the mixture was heated to reflux for 4 h. The mixture was allowed to cool to room temperature and concentrated. The mixture was diluted with $CH_2Cl_2$ and $H_2O$ and the organic phase was separated. The aqueous phase was re-extracted ($CH_2Cl_2$) and the combined organics were washed (saturated aqueous NaCl), dried ($MgSO_4$), filtered and concentrated to give a solid residue. The residue was purified by flash chromatography (EtOAc/$CH_2Cl_2$/hexanes 4:50:50 then 6:50:50 then 8:50:50) to give 4-(5-methylthiophen-2-yl)-1-trityl-1H-imidazole (6.15 g, 83%) as a colourless solid. $^1$H NMR (CDCl$_3$, 400 MHz) δ2.46 (d, J=0.9 Hz, 3H), 6.62-6.65 (m, 1H), 6.94 (d, J=1.4 Hz, 1H), 6.99 (d, J=3.5 Hz, 1H), 7.15-7.21 (m, 6H), 7.31-7.37 (m, 9H), 7.41 (d, J=1.4 Hz, 1H); $^{13}$C NMR (CDCl$_3$, 100 MHz)

δ15.3, 75.5, 116.1, 121.7, 125.5, 128.1, 128.1, 129.8, 135.6, 136.4, 137.8, 138.9, 142.2; HRMS (EI) m/z 406.1496 $C_{27}H_{22}N_2S$ $[M]^{+\cdot}$ requires 406.1498.

Example 2

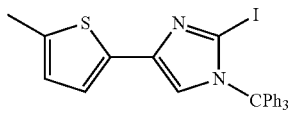

2-Iodo-4-(5-methylthiophen-2-yl)-1-trityl-1H-imidazole 2

A mixture of 4-(5-methylthiophen-2-yl)-1-trityl-1H-imidazole (2.20 g, 5.42 mmol) in THF (100 mL) was cooled to −78° C. $^{n}$BuLi mL of a 1.6 M solution in hexanes, 6.2 mmol) was added dropwise (~2 min) and the pale yellow solution was allowed to warm to −50° C. (over ~1 h) and then re-cooled to −78° C. $I_2$ (2.74 g, 10.4 mmol) was added and the mixture was allowed to warm to room temperature (over ~4 h) and stirred overnight. Saturated aqueous $NH_4Cl$ (2 mL) was added and the mixture was concentrated to ~10 mL. The mixture was diluted with EtOAc, $H_2O$, saturated aqueous $Na_2S_2O_3$ and the organic phase was separated. The aqueous phase was re-extracted (EtOAc) and the combined organics were washed (saturated aqueous NaCl), dried ($MgSO_4$), filtered and concentrated to give a residue. The residue was purified by flash chromatography (EtOAc/hexanes 5:95 then 15:85) to give 2-iodo-4-(5-methylthiophen-2-yl)-1-trityl-1H-imidazole 2 (1.72 g, 60%) as a colourless solid. $^1$H NMR ($CDCl_3$, 400 MHz) δ2.45 (s, 3H), 6.60-6.64 (m, 1H), 6.94 (s, 1H), 6.99 (d, J=3.5 Hz, 1H), 7.19-7.39 (m, 15H); $^{13}$C NMR ($CDCl_3$, 100 MHz) δ15.3, 90.6, 120.4, 122.3, 125.5, 125.6, 127.2, 128.1, 130.8, 134.2, 138.1, 138.2, 141.4, 146.8; HRMS (EI) m/z 532.0459 $C_{27}H_{21}N_2IS$ $[M]^{+\cdot}$ requires 532.0465.

Examples 3 and 4

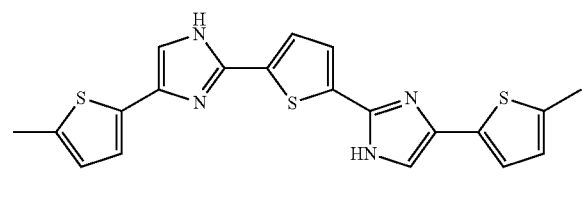

2,5-bis(4-(5-methylthiophen-2-yl)-1H-imidazol-2-yl)thiophene 4

A mixture of 2-iodo-4-(5-methylthiophen-2-yl)-1-trityl-1H-imidazole 2 (2.57 g, 4.83 mmol) and AcOH (3 mL) in MeOH (120 mL) was heated under reflux (2 h). The mixture was allowed to cool to room temperature and then concentrated to give a residue. The residue was taken up in toluene and concentrated to five a residue. The residue was diluted with $CH_2Cl_2$, $H_2O$, saturated aqueous $NaHCO_3$ and the organic phase was separated. The aqueous phase was re-extracted ($CH_2Cl_2$) and the combined organics were washed (saturated aqueous NaCl), dried ($MgSO_4$), filtered and concentrated to give a residue. The residue was purified by flash chromatography (EtOAc/hexanes 15:85 then 30:70 then 40:60) to give 2-iodo-4-(5-methylthiophen-2-yl)-1H-imidazole 3 (1.2 g, 86%) as a colourless solid. $^1$H NMR ($CDCl_3$, 400 MHz) □ 2.48 (d, J=1.0 Hz, 3H), 6.65-6.68 (m, 1H), 7.03 (d, J=3.5 Hz 1H), 7.14 (s, 1H).

A portion of 2-iodo-4-(5-methylthiophen-2-yl)-1H-imidazole 3 (940 mg, 3.25 mmol), thiophene-2,5-diboronic acid (250 mg, 1.46 mmol), $Na_2CO_3$ (780 mg, 7.40 mmol) in $H_2O$ (5 mL) and DMF (40 mL) was degassed ($N_2$ bubbling). $Pd(PPh_3)_4$ (85 mg) was added and the mixture was heated to reflux for 3 h. The mixture was allowed to cool to room temperature and concentrated. The mixture was diluted with EtOAc and $H_2O$ and the organic phase was separated. The aqueous phase was re-extracted (EtOAc) and the combined organics were washed (saturated aqueous NaCl), dried ($MgSO_4$), filtered and concentrated to give a residue. The residue was purified by flash chromatography (EtOAc/hexanes 35:65 then 50:50 then 75:25) to give 2,5-bis(4-(5-methylthiophen-2-yl)-1H-imidazol-2-yl)thiophene 4 (1.65 g, 27%) as a pale brown solid. $^1$H NMR [$(CD_3)_2SO$, 400 MHz] δ2.44 (s, 6H), 6.75 (s, 2H), 7.11 (d, J=3.0 Hz, 2H), 7.51 (br s, 4H), 12.65-12.85 (br s, 2H); HRMS (EI) m/z 408.0539 $C_{20}H_{16}N_4S_3$ $[M]^{+\cdot}$ requires 408.0532.

Example 5

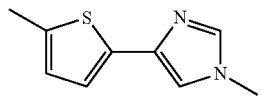

1-Methyl-4-(5-methylthiophen-2-yl)-1H-imidazole 5

To 4-(5)-iodoimidazole (12.1 g, 67.7 mmol) in THF (220 mL) at 0° C. was added (in portions, over 5 min) NaH (2.77 g of a 60% dispersion in mineral oil, 69.0 mmol). The mixture was stirred at 0° C. (15 min) and then at room temperature (20 min). The mixture was re-cooled to 0° C. and MeI (4.49 mL, 72.0 mmol) was added and the mixture was stirred (10 min) and then at room temperature (1 h). $H_2O$ (5 mL) was cautiously added and the mixture was concentrated (~10 mL). The mixture was diluted with $CH_2Cl_2$ and $H_2O$ and the organic phase was separated. The aqueous phase was re-extracted ($CH_2Cl_2$) and the combined organics were washed (saturated aqueous NaCl), dried ($MgSO_4$), filtered and concentrated to give a residue. The residue was taken up in DMF (100 mL) and a few drops of MeI was added. This mixture was heated to 75° C. (14 h).$H_2O$ (3 mL) was added and the mixture was concentrated to give a residue (12.9 g). To this residue (12.9 g) was added 5-methylthiophene-2-boronic acid pinacol ester (16.1 g, 72.0 mmol), $Na_2CO_3$ (20.8 g, 0.198 mol) in $H_2O$ (50 mL) and DMF (200 mL) and the mixture was degassed ($N_2$ bubbling). $Pd(PPh_3)_4$ (1.0 g) was added and the mixture was heated to reflux for 3 h.

The mixture was allowed to cool to room temperature and concentrated. The mixture was diluted with CH$_2$Cl$_2$ and H$_2$O and the organic phase was separated. The aqueous phase was re-extracted (CH$_2$Cl$_2$) and the combined organics were washed (saturated aqueous NaCl), dried (MgSO$_4$), filtered and concentrated to give a residue. The residue was purified by flash chromatography (EtOAc/hexanes 40:50 then 50:50 then 60:40 then 70:30) to give 1-methyl-4-(5-methylthiophen-2-yl)-1H-imidazole 5 (4.23 g, 38%) as a colourless solid. $^1$H NMR (CDCl$_3$, 400 MHz) δ2.45 (s, 3H), 3.64 (s, 3H), 6.62-6.656 (m, 1H), 6.97 (s, 1H), 7.02 (d, J=3.5 Hz, 1H), 7.40 (s, 1H); HRMS (EI) m/z 178.0556 C$_9$H$_{10}$N$_2$S [M]$^{+\cdot}$ requires 178.0559.

Example 6

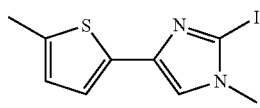

2-Iodo-1-methyl-4-(5-methylthiophen-2-yl)-1H-imidazole 6

A mixture of 1-methyl-4-(5-methylthiophen-2-yl)-1H-imidazole 5 (2.36 g, 13.3 mmol) in THF (0.100 mL) was cooled −78° C. $^n$BuLi (9.53 mL of a 1.6 M solution in hexanes, 15.2 mmol) was added dropwise (~2 min) and the pale yellow solution was allowed to warm to −40° C. (over ~1 h) and then re-cooled to −78° C. I$_2$ (2.74 g, 10.4 mmol) was added and the mixture was allowed to warm to room temperature (over ~2 h) and stirred overnight. Saturated aqueous NH$_4$Cl (2 mL) was added and the mixture was concentrated to ~10 mL. The mixture was diluted with CH$_2$Cl$_2$. H$_2$O, saturated aqueous Na$_2$S$_2$O$_3$ and the organic phase was separated. The aqueous phase was re-extracted (CH$_2$Cl$_2$) and the combined organics were washed (saturated aqueous NaCl), dried (MgSO$_4$), filtered and concentrated to give a residue. The residue was purified by flash chromatography (EtOAc/hexanes 10:90 then 15:85 then 25:75) to give 2-iodo-1-methyl-4-(5-methylthiophen-2-yl)-1H-imidazole 6 (3.37 g, 84%) as a colourless solid. $^1$H NMR (CDCl$_3$, 400 MHz) δ2.46 (d, J=0.8 Hz, 3H), 3.59 (s, 3H), 6.62-6.66 (m, 1H), 7.04 (d, J=3.5 Hz, 1H), 7.11 (s, 1H); $^{13}$C NMR (CDCl$_3$, 100 MHz) δ15.3, 36.8, 91.0, 118.7, 122.2, 125.5, 134.3, 138.1, 140.5; HRMS (EI) m/z 303.9533 C$_9$H$_9$N$_2$IS [M]$^{+\cdot}$ requires 303.9526.

Example 7

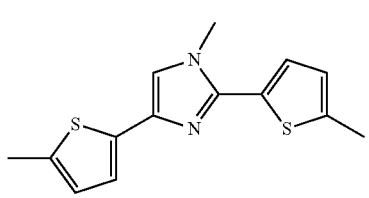

1-Methyl-2,4-bis(5-methylthiophen-2-yl)-1H-imidazole 7

A mixture of 2-iodo-1-methyl-4-(5-methylthiophen-2-yl)-1H-imidazole 6 (1.31 g, 4.31 mmol), 5-methylthiophene-2-boronic acid pinacol ester (1.35 g, 6.03 mmol), Na$_2$CO$_3$ (1.80 g, 17.2 mmol) in H$_2$O (10 mL) and DMF (40 mL) was degassed (N$_2$ bubbling). Pd(PPh$_3$)$_4$ (125 mg) was added and the mixture was heated to reflux for 5 h. The mixture was allowed to cool to room temperature and concentrated. The mixture was diluted with EtOAc and H$_2$O and the organic phase was separated. The aqueous phase was re-extracted (EtOAc) and the combined organics were washed (saturated aqueous NaCl), dried (MgSO$_4$), filtered and concentrated to give a residue. The residue was purified by flash chromatography (EtOAc/hexanes 10:90 then 15:85 then 20:80) to give 1-methyl-2,4-bis(5-methylthiophen-2-yl)-1H-imidazole 7 (930 mg, 79%) as a colourless solid. A portion of this material was further purified by, firstly, recrystallisation (EtOAc/hexanes) and, secondly, by sublimation (130° C., 10$^{-6}$ mBar): m.p. 138-140° C. $^1$H NMR (CDCl$_3$, 400 MHz) δ2.48 (d, J=0.7 Hz, 3H), 2.51 (d, J=0.7 Hz, 3H), 3.76 (s, 3H), 6.64-6.67 (m, 1H), 6.73-6.77 (m, 1H), 7.00 (s, 1H), 7.10 (d, J=3.4 Hz, 1H), 7.14 (d, J=3.4 Hz, 1H); $^{13}$C NMR (CDCl$_3$, 100 MHz) δ15.2, 15.3, 34.5, 117.0, 122.1, 125.5, 125.6, 126.7, 136.3, 137.7, 141.5, 142.4; HRMS (EI) m/z 274.0589 C$_{14}$H$_{14}$N$_2$S$_2$ [M]$^{+\cdot}$ requires 274.0593.

Example 8

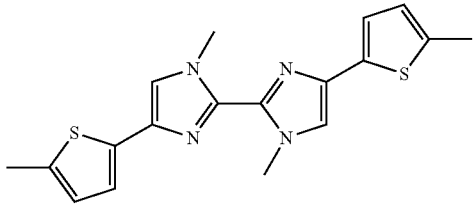

1,1'-Dimethyl-4,4'-bis(5-methylthiophen-2-yl)-1H,1'H-2,2'-biimidazole 8

A mixture of 2-iodo-1-methyl-4-(5-methylthiophen-2-yl)-1H-imidazole 6 (1.78 g, 5.86 mmol), 1,10-phenanthroline (1.11 g, 6.16 mmol) and Cs$_2$CO$_3$ (4.01 g, 12.3 mmol) in DMF (12 mL) was degassed (N$_2$ bubbling). CuI (1.17 g, 6.16 mmol), was added and the mixture was heated to 105° C. for 40 h and then allowed to cool to room temperature. The mixture was filtered through Celite washing with EtOAc and the combined filtrate and washings were concentrated. The residue was taken up in CH$_2$Cl$_2$ and H$_2$O and the organic phase was separated. The aqueous phase was re-extracted (CH$_2$Cl$_2$) and the combined organics were washed (saturated aqueous NaCl), dried (MgSO$_4$), filtered and concentrated to give a residue. The residue was purified by flash chromatography (EtOAc/CH$_2$Cl$_2$ 0:100 then 2:98 then 4:96) to give 1,1'-dimethyl-4,4'-bis(5-methylthiophen-2-yl)-1H,1'H-2,2'-biimidazole 8 (501 mg, 48%) as a colourless solid. A portion of this material was further purified by sublimation (180° C., 10$^{-6}$ mBar): m.p. 220-228° C. (DSC) $^1$H NMR (CDCl$_3$, 400 MHz) δ2.49 (d, J=0.8 Hz, 6H), 4.09 (s, 6H), 6.66-6.69 (m, 2H), 7.07 (s, 2H), 7.08 (d, J=3.4 Hz, 2H); $^{13}$C NMR (CDCl$_3$, 100 MHz) δ15.3, 35.6, 117.4, 121.7, 125.6, 135.4, 135.9, 137.8, 137.9; HRMS (EI) m/z 354.0963 C$_{18}$H$_{18}$N$_4$S$_2$ [M]$^{+\cdot}$ requires 354.0967.

Example 9

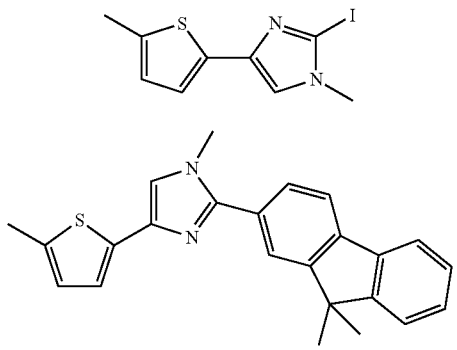

2-(9,9-dimethyl-9H-fluoren-2-yl)-1-methyl-4-(5-methylthiophen-2-yl)-1H-imidazole 9

A mixture of 2-iodo-1-methyl-4-(5-methylthiophen-2-yl)-1H-imidazole 6 (1.26 g, 4.16 mmol), (9,9-dimethyl-9H-fluoren-2-yl)boronic acid (1.19 g, 5.00 mmol), Na$_2$CO$_3$ (2.20 g, 20.8 mmol) in H$_2$O (10 mL) and DMF (40 mL) was degassed (N$_2$ bubbling). Pd(PPh$_3$)$_4$ (120 mg, 0.10 mmol) was added and the mixture was heated to reflux for 2 h. The mixture was allowed to cool to room temperature and concentrated. The mixture was filtered through Celite washing with CH$_2$Cl$_2$ and the combined filtrate and washings were concentrated. The residue was taken up in CH$_2$Cl$_2$ and H$_2$O and the organic phase was separated. The aqueous phase was re-extracted (CH$_2$Cl$_2$) and the combined organics were washed (saturated aqueous NaCl), dried (MgSO$_4$), filtered and concentrated to give a residue. The residue was purified by flash chromatography (EtOAc/hexanes 5:95 then 10:90 then 12:88) to give 2-(9,9-dimethyl-9H-fluoren-2-yl)-1-methyl-4-(5-methylthiophen-2-yl)-1H-imidazole 9 (1.19 g, 76%) as a colourless solid. A portion of this material was further purified by, firstly, recrystallisation (EtOAc/hexanes) and, secondly, by sublimation (180° C., 10$^{-6}$ mBar): m.p. 188-191° C. (DSC)$^1$H NMR (CDCl$_3$, 400 MHz) δ1.53 (s, 6H), 2.50 (d, J=0.6 Hz, 3H), 3.76 (s, 3H), 6.68-6.71 (m, 1H), 7.11 (s, 1H), 7.13-7.19 (m, 1H), 7.32-7.40 (m, 2H), 7.43-7.49 (m, 1H), 7.58 (dd, J 1.4, 8.0 Hz, 1H), 7.73-7.81 (m, 3H); $^{13}$C NMR (CDCl$_3$, 100 MHz) δ15.3, 27.1, 34.6, 47.0, 117.1, 119.8, 120.3, 122.1, 122.7, 123.6, 125.6, 127.0, 127.7, 137.8, 138.5, 139.9, 148.3, 153.9, 154.0; HRMS (EI) m/z 370.1490 C$_{24}$H$_{22}$N$_2$S [M]$^{+\cdot}$ requires 370.1498.

Example 10

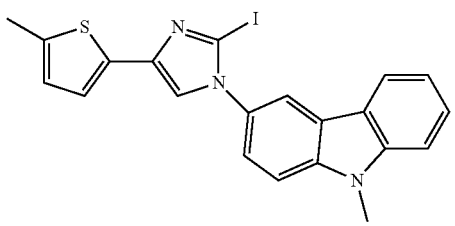

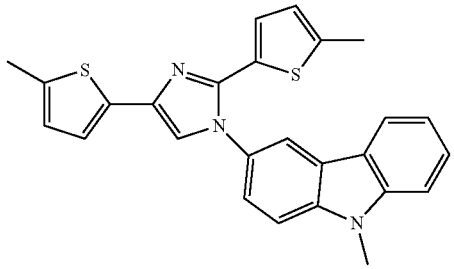

3-(2,4-bis(5-methylthiophen-2-yl)-1H-imidazol-1-yl)-9-methyl-9H-carbazole 11

A mixture of 3-(2-iodo-4-(5-methylthiophen-2-yl)-1H-imidazol-1-yl)-9-methyl-9H-carbazole 10 (920 g, 2.0 mmol), 5-methylthiophene-2-boronic acid pinacol ester (880 mg, 3.9 mmol), Na$_2$CO$_3$ (1.03 g, 9.81 mmol) in H$_2$O (5 mL) and DMF (20 mL) was degassed (N$_2$ bubbling). Pd(PPh$_3$)$_4$ (60 mg) was added and the mixture was heated to reflux for 8 h. The mixture was allowed to cool to room temperature and concentrated. The residue was washed with H$_2$O (3 times) and EtOAc (1 time). The solid material was transferred to a soxlet apparatus and the material extracted with EtOAc. The organic extract was concentrated to ~10 mL and the solid material was collected and recrystallised (EtOAc) to give 3-(2,4-bis(5-methylthiophen-2-yl)-1H-imidazol-1-yl)-9-methyl-9H-carbazole 11 (1.19 g, 76%) as colourless crystals. A portion of this material was further purified by sublimation (220° C., 10$^{-6}$ mBar): m.p. 248-255° C. (DSC)$^1$H NMR (CDCl$_3$, 400 MHz) δ 2.33 (s, 3H), 2.51 (d, J=0.6 Hz, 3H), 3.94 (s, 3H), 6.48 (br s, 1H), 6.72 (d, J=2.5 Hz, 1H), 7.22 (s, 1H), 7.30 (t, 7.6 Hz, 1H), 7.43 (dd, J 2.0, 8.6 Hz, 1H), 7.49 (d, 8.5 Hz, 2H), 7.57 (dt, J 1.0, 7.6 Hz, 1H), 8.08 (d, 7.7 Hz, 1H), 8.10 (d, J=1.8 Hz, 1H); $^{13}$C NMR (CDCl$_3$, 100 MHz) δ 15.1, 15.4, 109.0, 109.2, 117.9, 119.2, 119.8, 120.8, 122.2, 123.3, 124.5, 125.9, 126.1, 126.9, 141.1, 141.8, 142.6; HRMS (EI) m/z 439.1163 C$_{24}$H$_{22}$N$_2$S [M]$^{+\cdot}$ requires 439.1171.

Example 11

Device Properties

Device properties based on two selected materials 53 and 5, and one commercial material (NPD) for the reference purpose. A summary of the demonstrated, light emitting devices is shown in Table 1.

The device was manufactured as below;

Device A; Structure: 145 nm ITO (anode)/40 nm PEDOT: PSS (hole-injection layer)/30 nm Material 53 (hole-transport layer)/30 nm Alq$_3$ (emission layer)/1 nm LiF (electron transporting layer)/100 nm Al (cathode); in accordance with FIG. 4

Process:

PEDOT: PSS layer was spin coated as a hole injection layer on top of pre-cleaned ITO substrate in the air. After baking at 150° C. for 15 minutes, substrates are then transferred to a vacuum chamber for thermal deposition of the rest of layers, including the hole-transport layer, emission layer and the cathode, under a vacuum pressure of 1×10$^{-5}$ Pa. An encapsulation process with another cover glass was employed with a desiccant inside the device and sealed by the uv cured epoxy to avoid the contact with oxygen and moisture.

Device B; Device B was fabricated using compound 5 instead of compound 53 under the same conditions as for Device A.

Device C; Device C was fabricated using compound NPD instead of compound 53 under the same conditions as for Device A.

The device performance data is shown in Table 1. Light emitting devices showed a current efficiency of 0.4 cd/A at a current density of 25.0 mA/cm² and a brightness of 100 cd/m² for material 53. OLEDs showed a maximum current efficiency of 2.1 cd/A is at a current density of 5.1 mA/cm² and a brightness of 100 cd/m² for material 5. For NPD material, OLEDs showed a maximum current efficiency of 1.8 cd/A at a current density of 5.6 mA/cm² and a brightness of 100 cd/m² for material NPD. The colour is green and the CIE coordinate is (0.34, 0.54), (0.33, 0.56), and (0.34, 0.55) respectively.

TABLE 1

| | Example material | CIE | Efficiency (cd/A) | Brightness (cd/m²) | Voltage (V) | Current Density (mA/cm²) |
|---|---|---|---|---|---|---|
| Device A | 53 | (0.34, 0.54) | 0.4 | 100.0 | 5.0 | 25.0 |
| Device B | 5 | (0.33, 0.56) | 2.0 | 100.0 | 7.5 | 5.1 |
| Device C | NPD | (0.34, 0.55) | 1.8 | 100.0 | 3.0 | 5.6 |

Device A, B and C share the same device structures but use different materials as examples
Structure: 145 nm ITO (anode)/40 nm PEDOT: PSS (hole-injection layer)/30 nm Material 53 or 5 or NPD (hole-transport layer)/30 nm Alq₃ (emission layer)/1 nm LiF (electron transporting layer)/100 nm Al (cathode); in accordance with FIG. 4

The invention claimed is:

1. An organic electroluminescent device comprising:

a pair of electrodes comprising an anode and a cathode, and one or more layers of organic compound arranged between the pair of electrodes, wherein the organic compound layer, or one or more of the organic compound layers, comprises a compound represented by the following formula:

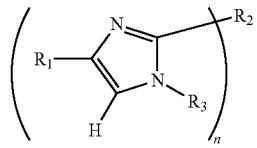

wherein:

$R_1$ to $R_2$, are the same or different and are each independently selected from the group consisting of: substituted or unsubstituted aryl group or substituted or unsubstituted heterocyclic group;

$R_3$ is selected from the group consisting of: substituted or unsubstituted aryl group, substituted or unsubstituted heterocyclic group, substituted or unsubstituted alkyl group or cyano group;

when n=1, $R_1$ or $R_2$ is a substituted or unsubstituted thiophene group; or when n=2, the compound is represented by the formula:

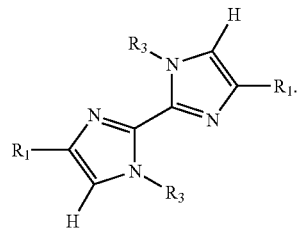

2. A device according to claim 1, wherein the compound is of formula:

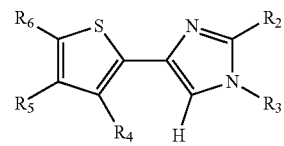

$R_2$ is selected from the group consisting of: substituted or unsubstituted aryl group or a substituted or unsubstituted heterocyclic group;

$R_3$ is selected from the group consisting of: substituted or unsubstituted aryl group or a substituted or unsubstituted heterocyclic group, substituted or unsubstituted alkyl group;

$R_4$ to $R_6$ are the same or different, and are each independently selected from the group consisting of hydrogen atom, halogen atom, nitro group, ketone group, amide group, cyano group, carboxylate group, sulfonate group, substituted or unsubstituted aryl group, substituted or unsubstituted alkyl group and substituted or unsubstituted heterocyclic group, or are pairs of substituents in which $R_4$ and $R_5$, or $R_5$ and $R_6$ together form a substituted or unsubstituted cyclic group.

3. A device according to claim 1, wherein the compound is of formula:

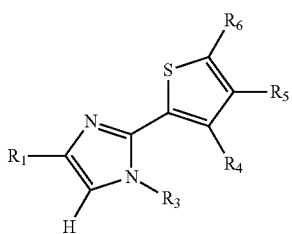

R₁ is selected from the group consisting of: substituted or unsubstituted aryl group or a substituted or unsubstituted heterocyclic group;

R₃ is selected from the group consisting of: substituted or unsubstituted aryl group or a substituted or unsubstituted heterocyclic group, substituted or unsubstituted alkyl group;

R₄ to R₆ are the same or different, and are each independently selected from the group consisting of hydrogen atom, halogen atom, nitro group, ketone group, amide group, cyano group, carboxylate group, sulfonate group, substituted or unsubstituted aryl group, substituted or unsubstituted alkyl group and substituted or unsubstituted heterocyclic group, or pairs of substituents in which R₄ and R₅, or R₅ and R₆ together form a substituted or unsubstituted cyclic group.

4. A device according to claim 1, wherein the compound is of formula:

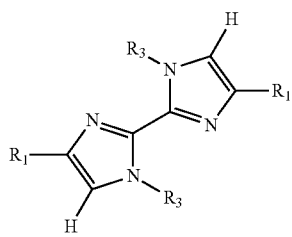

R₁ is selected from the group consisting of: substituted or unsubstituted aryl group or a substituted or unsubstituted heterocyclic group;

R₃ is selected from the group consisting of: substituted or unsubstituted aryl group or a substituted or unsubstituted heterocyclic group, substituted or unsubstituted alkyl group.

5. A device according to claim 1, wherein the aryl group is monocyclic.

6. A device according to claim 1, wherein the aryl group is polycyclic.

7. A device according to claim 1, wherein R₁ to R₆ are each independently selected from substituted or unsubstituted heterocyclic groups.

8. A device according to claim 1, wherein the heterocyclic groups are polyheterocyclic.

9. A device according to claim 1, wherein R₃ is a substituted or unsubstituted alkyl group.

10. A device according to claim 1, wherein R₃ is a substituted or unsubstituted monocyclic or polycyclic aromatic compound with 2 or more sites for attachment.

11. A device according to claim 1, wherein R₃ is a substituted or unsubstituted monoheterocyclic or polyheterocyclic compound with 2 or more sites for attachment.

12. A device according to claim 1, wherein the device is a stacked organic electroluminescent device.

13. A device according to claim 1, wherein the device comprises a display.

14. A device according to claim 1, wherein the device comprises a light source.

15. A device according to claim 1, wherein the light emitting layer comprises a host material and a phosphorescent material and wherein the host material comprises the organic compound.

16. A device according to claim 1 wherein the light emitting layer comprises a host material and a phosphorescent material and wherein the phosphorescent material comprises an iridium metal, an osmium metal or a platinum metal.

17. A device according to claim 1 wherein the light emitting layer comprises a host material and a phosphorescent material and wherein the phosphorescent material is a light emitting material having a metal-carbene bond.

18. An organic electroluminescent device having at least one layer selected from a hole injection layer or a hole transporting layer, the layer comprising a compound represented by the following formula:

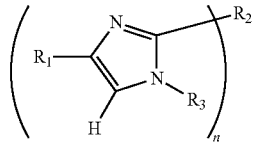

wherein:

R₁ to R₂, are the same or different and are each independently selected from the group consisting of: substituted or unsubstituted aryl group or substituted or unsubstituted heterocyclic group; and R₃ is selected from the group consisting of: substituted or unsubstituted aryl group, substituted or unsubstituted heterocyclic group, substituted or unsubstituted alkyl group or cyano group;

wherein when n=1, R₁ or R₂ is a substituted or unsubstituted thiophene group; or when n=2, the compound is represented by the formula:

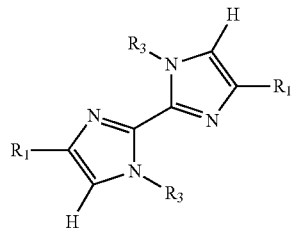

wherein when the device includes a hole transporting layer that comprise the compound, the compound may function as the hole transporting layer or as a dopant within the hole transporting layer.

19. A method of making an electroluminescent device, comprising:

arranging a layer comprising an organic compound between a pair of electrodes comprising an anode and a cathode, wherein the organic compound is represented by the following formula:

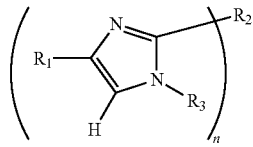

wherein:

R₁ to R₂, are the same or different and are each independently selected from the group consisting of: substituted or unsubstituted aryl group or substituted or unsubstituted heterocyclic group;

R₃ is selected from the group consisting of: substituted or unsubstituted aryl group, substituted or unsubstituted heterocyclic group, substituted or unsubstituted alkyl group or cyano group;
when n=1, R₁ or R₂ is a substituted or unsubstituted thiophene group; or
when n=2, the compound is represented by the formula:
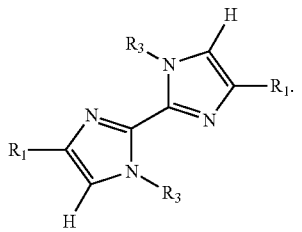
* * * * *